(12) United States Patent
Bonutti et al.

(10) Patent No.: US 12,167,984 B2
(45) Date of Patent: Dec. 17, 2024

(54) ROBOTIC SYSTEMS, OPERATING ROOM SYSTEMS, INSULATED CONDUCTOR INCLUDING BIOLOGICALLY ACTIVE MATERIAL, MICROPLASTIC FILTER, AND COMBINATIONS THEREOF

(71) Applicant: P Tech, LLC, Effingham, IL (US)

(72) Inventors: Peter M. Bonutti, Manalapan, FL (US); Justin E. Beyers, Effingham, IL (US)

(73) Assignee: P TECH, LLC, Manalapan, FL (US)

( * ) Notice: Subject to any disclaimer, the term of this patent is extended or adjusted under 35 U.S.C. 154(b) by 0 days.

(21) Appl. No.: 17/495,555

(22) Filed: Oct. 6, 2021

(65) Prior Publication Data
US 2022/0133572 A1    May 5, 2022

Related U.S. Application Data

(60) Provisional application No. 63/088,369, filed on Oct. 6, 2020.

(51) Int. Cl.
*A61G 13/10* (2006.01)
*A61B 5/00* (2006.01)
(Continued)

(52) U.S. Cl.
CPC .......... *A61G 13/10* (2013.01); *A61B 5/01* (2013.01); *A61B 5/0816* (2013.01); *A61B 5/1113* (2013.01); *A61B 5/6892* (2013.01); *A61B 34/37* (2016.02); *A61B 90/08* (2016.02); *A61B 90/361* (2016.02); *A61B 90/37* (2016.02);
(Continued)

(58) Field of Classification Search
CPC ...... A61G 13/10; A61G 13/02; A61G 13/101; A61G 13/102; A61B 2090/571; A61B 5/1112; A61B 5/1113; A61B 34/37; A61B 90/08; A61B 90/361; A61B 90/37; B25J 13/06; G16H 50/20
See application file for complete search history.

(56) References Cited

U.S. PATENT DOCUMENTS 6,824,108 B2   11/2004   Bonutti
9,486,227 B2 * 11/2016   Bonutti .............. A61B 17/8805
(Continued)

*Primary Examiner* — Kevin T Truong
*Assistant Examiner* — Diana Jones
(74) *Attorney, Agent, or Firm* — Stinson LLP

(57) ABSTRACT

This disclosure provides an enhanced operating table and room, an insulated conductor, and a filtration system. The table includes an attachment, controlling parameters during surgery, a control, and a console. The attachment is moveable relative to at least one reference point. The console allows monitoring parameters during surgery. The room includes sensors integrated throughout and a data module in communication with the sensors. The data module receives data from the plurality of sensors, stores the received data in memory, and analyzes and processes the stored data. The insulated conductor includes an electrical conductor and an insulator. The insulator partially electrically or thermally insulates the electrical conductor. The filtration system removes particles within a fluid A transducer generates a pressure gradient to promote the particles to flow. Alternatively, the filtration system can include a robotic system. The robotic system charges particles such that the particles within the fluid adhere.

19 Claims, 27 Drawing Sheets

(51) Int. Cl.

| | | |
|---|---|---|
| *A61B 5/01* | (2006.01) | |
| *A61B 5/08* | (2006.01) | |
| *A61B 5/11* | (2006.01) | |
| *A61B 34/37* | (2016.01) | |
| *A61B 90/00* | (2016.01) | |
| *A61B 90/50* | (2016.01) | |
| *A61G 13/02* | (2006.01) | |
| *B25J 1/00* | (2006.01) | |
| *B25J 9/16* | (2006.01) | |
| *B25J 13/06* | (2006.01) | |
| *C02F 1/36* | (2023.01) | |
| *C02F 1/42* | (2023.01) | |
| *G06F 3/01* | (2006.01) | |
| *G16H 50/20* | (2018.01) | |

(52) U.S. Cl.
CPC .............. *A61B 90/50* (2016.02); *A61G 13/02* (2013.01); *B25J 1/00* (2013.01); *C02F 1/36* (2013.01); *C02F 1/42* (2013.01); *G06F 3/011* (2013.01); *G16H 50/20* (2018.01); *B25J 9/1697* (2013.01); *B25J 13/06* (2013.01)

(56) References Cited

U.S. PATENT DOCUMENTS

| | | | |
|---|---|---|---|
| 10,231,739 B1 | 3/2019 | Bonutti | |
| 10,765,484 B2 | 9/2020 | Bonutti et al. | |
| 2006/0276775 A1* | 12/2006 | Rosenberg | A61B 17/0469 606/1 |
| 2011/0279325 A1* | 11/2011 | Riesner | H04N 5/222 342/457 |
| 2014/0188132 A1* | 7/2014 | Kang | A61B 6/4441 606/130 |
| 2015/0094736 A1* | 4/2015 | Malackowski | A61B 5/0036 606/130 |
| 2016/0374771 A1* | 12/2016 | Mirbagheri | A61G 13/06 606/130 |
| 2017/0252921 A1* | 9/2017 | Hynna | A61B 90/98 |
| 2017/0296293 A1* | 10/2017 | Mak | G16H 30/40 |
| 2018/0132949 A1* | 5/2018 | Merette | G06T 11/60 |
| 2019/0021800 A1* | 1/2019 | Crawford | A61B 6/547 |
| 2019/0117310 A1* | 4/2019 | Hiratsuka | A61B 34/70 |
| 2020/0030991 A1* | 1/2020 | Bailey | A61B 34/20 |
| 2020/0138534 A1* | 5/2020 | Garcia Kilroy | A61G 13/08 |

* cited by examiner

| People | Sterile Field Floor Sensor | | | | | | | | | People | Non-Sterile Field Floor Sensor | | | | | | Patient Vital Monitor | | | | | Patient Bed Monitor | | Environmental Sensor | |
|---|---|---|---|---|---|---|---|---|---|---|---|---|---|---|---|---|---|---|---|---|---|---|---|---|---|
| | Person 1 | | | Person 2 | | | Person 3 | | | | Person 1 | | | Person 2 | | | | | | | | | | | |
| | Location | Alert To Physician | Alert From Physician | Location | Alert To Physician | Alert From Physician | Location | Alert To Physician | Alert From Physician | | Location | Alert To Physician | Alert From Physician | Location | Alert To Physician | Alert From Physician | Heart Rate | Breath Rate | Oxygen Level | Blood Pressure | Movement | Skin Temp | Room Temp | Humidity | Oxygen level |
| 8 | | | | | | | | | | 2 | | | | | | | | | | | | | | | |
| 3 | F1 | Not Active | Not Active | B2 | Not Active | Not Active | A1 | Not Active | Not Active | 2 | I1 | Not Active | Not Active | H1 | Not Active | Not Active | 80 | 16 | 80 | 120/80 | No | 38.6 | 66.6 | 26.0% | 32.2% |
| 3 | F2 | Not Active | Not Active | B3 | Not Active | Not Active | A1 | Not Active | Not Active | 2 | I1 | Not Active | Not Active | H2 | Not Active | Not Active | 80 | 16 | 81 | 120/80 | No | 38.6 | 66.7 | 26.1% | 32.1% |
| 3 | F3 | Active | Not Active | B4 | Not Active | Not Active | A1 | Not Active | Not Active | 2 | I1 | Active | Not Active | H3 | Not Active | Not Active | 80 | 16 | 80 | 120/80 | No | 38.7 | 66.6 | 26.0% | 32.1% |

FIG. 9

ROBOTIC SYSTEMS, OPERATING ROOM SYSTEMS, INSULATED CONDUCTOR INCLUDING BIOLOGICALLY ACTIVE MATERIAL, MICROPLASTIC FILTER, AND COMBINATIONS THEREOF

BACKGROUND OF THE DISCLOSURE

With the high demand for improving patient surgical outcomes, along with controlling overhead cost without sacrificing patient satisfaction, hospitals need to analyze what environmental conditions, amount of personnel, and review surgical practices to develop the most efficient surgical protocols. Using a connected surgical room, would allow for data collection, which would further be used in improving surgical protocols with data backed evidence. Currently there are products that collect patient vitals, beds that track patient breathing patterns and heart rate, thermostats that measure environmental conditions and other patient monitoring devices. However, the major problem with all the data collection is that each device collects and reports the data independently. Without a direct correlation between each device, the data becomes less useful during analysis for surgical performance evaluation. There are also additional issues with how much data is stored and the memory space required to store this data.

In other aspects, some known consumer devices include one or more electrical components that create or are subjected to an electrical field, a magnetic field, and/or an electromagnetic field. During use, such components may be subjected to and/or generate heat. Additionally, such components may be subjected to and/or generate a corrosive substance. Known means for regulating and/or maintaining such components are ineffective or incompatible in various scenarios.

Further, plastic pollution in our marine environment is taking place on a staggering scale with 9.5 million tons of new plastic waste flowing into the ocean each year. Plastics pollution can be encountered in two forms: large plastic wastes and small plastic particulates below 5 millimeters (mm) in size named microplastics. For example, washing synthetic textiles creates microplastics through abrasion and shedding of fibers. Microplastics may be divided into primary microplastics, which are purposefully manufactured, and secondary microplastics, which are created when larger plastic pieces degrade. While pollution from large plastics can be addressed by recycling and other solid waste management strategies, these same strategies do not address microplastics. These plastics are extremely small and difficult to filter, as fine mesh filters are slow and tend to clog.

SUMMARY

The present disclosure provides a robotically enhanced operating table, an enhanced operating room, an insulated conductor, and a filtration system. The operating table includes an attachment that controls at least one parameter during surgery and is releasably affixed to at least a portion of the operating table. The operating table further includes a control and a console. The control is operably connected to the attachment, allowing an attachment to be moveable relative to at least one reference point. The console is connected to the attachment and the control, allowing an operator to monitor at least one parameter during surgery. The enhanced operating room for assessing surgical conditions includes a room for performing surgical procedures, a plurality of sensors integrated throughout the room, and a data module in communication with the sensors. The sensors measure a plurality of parameters associated with the room as data. The data module receives the data from the plurality of sensors, stores the received data in memory of the data module, and analyzes and processes the stored data with a processor of the data module. The insulated conductor includes an electrical conductor and an insulator. The electrical conductor channels electricity to and from at least one electively conductive material. The electricity channeled powers a target. The insulator couples to at least a portion of a surface of the electrical conductor, such that the insulator partially electrically or thermally insulates the electrical conductor. The filtration system removes particles within a fluid and includes a body that has a plurality of inner surfaces, an inlet, and an outlet. The inner surfaces define at least one channel. The channels are oriented in a direction that enables filtration of particles within the fluid. The filtration system further includes a transducer. The transducer generates a pressure gradient within the body to promote the particles to flow through the channels of the body. Alternatively, the filtration system can include a body and a robotic system. The robotic system charges particles such that the particles within the fluid adhere. The adhered particles are collectively removed through an outlet of the body.

BRIEF DESCRIPTION OF THE DRAWINGS

FIG. 9 is a performance report produced by the sensors.

DETAILED DESCRIPTION OF THE DISCLOSURE

Robotic Systems

Robotic systems additional related systems and methods of use in various medical applications are shown and described throughout the drawings and below. These systems and methods are constructed according to the teachings of the present disclosure and are not limiting. Variations may be constructed based on the below teachings. Moreover, the teachings of one embodiment may be readily used in another embodiment and combined in any suitable manner to enhance the systems.

Figure 1:
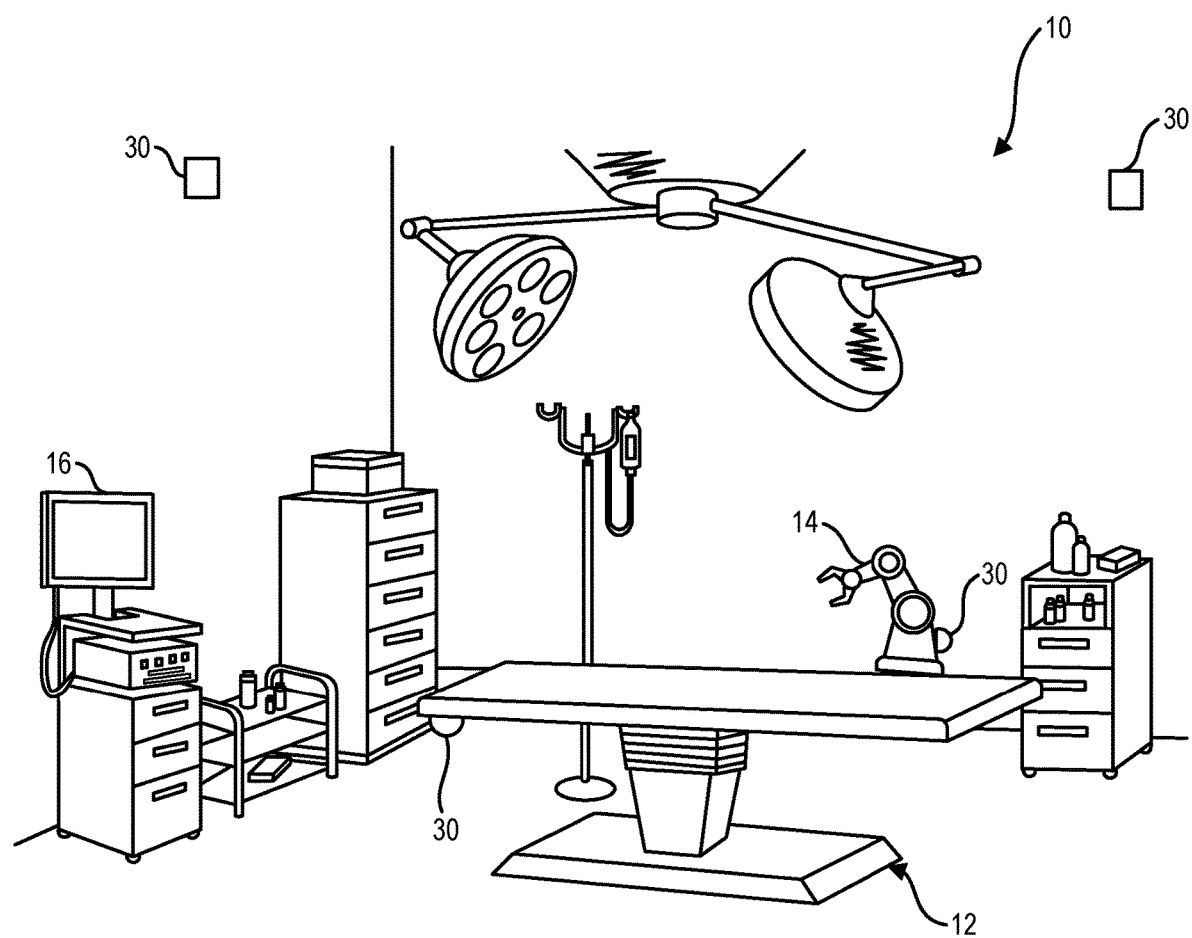
FIG. 1 is an illustration of an operating room including a robotic system of the present disclosure.
Figure 2:
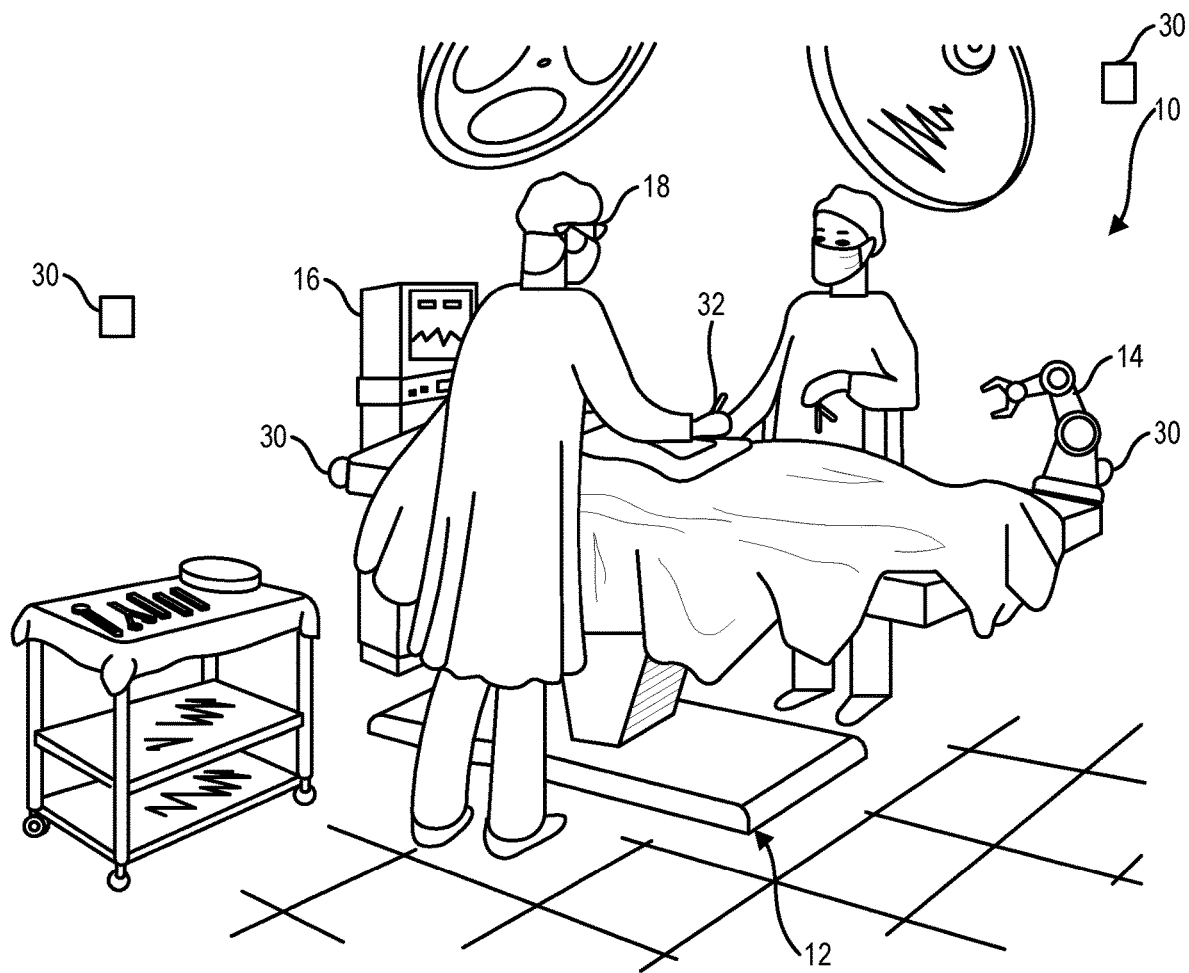
FIG. 2 is another illustration of an operating room including the robotic system and showing individuals operating on a patient.

In one such disclosure, and with reference to FIGS. 1 and 2, a robotic system is generally indicated at 10. The robotic system includes a robotic or robotically enhanced operating table generally indicated at 12. The operating table may include one or more attachments 14 configured to affect precise movements of one or more body parts of a subject lying on the operating table. The one or more attachments 14 may include retractors for engaging with the subject's body to position one or more parts of the body on the operating table. The attachments 14 may be assembled as one unit with the operating table 12, or the attachments may be separate components arranged on or around the operating table. For instance, the attachments 14 may be add-on/bolt-on features to an existing operating table. Thus, the attachments 14 may not be fixed or locked to the operating table. The one or more attachments 14 on the operating table 12 may also be controlled from a central console 16 operated by the physician/surgeon. In one embodiment, this is an automatic function of the operating table 12 with the retractor system/assistant system as all one fixed unit. This could be used in human surgery and could be used in other procedures such as veterinary procedures on animals. It could also be used in non-surgical applications for specific procedures such as exoskeletal, prosthesis, and the other procedures. In one embodiment, multiple devices may be attached to the operating table 12 and be controlled from the same robotic console 16 that the surgeon is controlling. Alternatively, the control can be performed with manual systems.

The one or more attachments 14 may be operated to hold the subject's body part (e.g., leg), move the body part a desired amount to locate the body part in a desired position, apply traction to the body part at a desired amount (e.g., force), apply a desired amount (e.g., degree) of torque to the body part, and/or apply a desired amount of push force from an external or internal surface of the body. For example, the attachments 14 may allow for precise movement of the subject's shoulder relative to another, or the attachments may extend or flex the subject's belly. Additionally, the attachments 14 may apply an external pressure (e.g. pneumatic pressure) on the subject's abdomen and/or right upper quadrant. In this instance, the attachment 14 may push the right upper quadrant closer or further away from the physician or an otherwise identified reference point. It is further envisioned that one or more attachments 14 can be used to move a subject's body part closer to a reference point such as a subject's arm or a separate robotic arm attachment. The attachments may also move structures closer to or further away from a reference point. In surgical applications, this functionality enhances the surgical visibility by moving obstructing structures away from the surgical site. Still other attachments may be used for controlling pressure, temperature, humidity, etc. in a medical room while also using the one or more attachments 14 to position or move the parts of the subject's body.

In a further example, when a subject's knee is extended, the popliteal vein, artery, and nerve are located closer to the back of the knee. Therefore, during surgical procedures involving access to the back of the knee, it may be desirable to operate with the knee in flexion as the tissues are more relaxed and thus move way from the back of the knee making it safer for the surgeon to perform the procedure. The one or more attachments 14 allow for incremental flexion or extension of the subject's leg to orient the leg in the preferred position. For example, flexion/extension is affected on the order of millimeters or fractions of degrees to enhance the safety factor and deliver the appropriate body part to the desired location.

In yet a further example, the one or more attachments 14 may be operated to expand an endotracheal tube to push the endotracheal tube closer or further away from the subject's heart. One or more attachments 14 could be directed down the patient's bronchi and then the attachment is inflated or mechanically pushed or magnetically pushed to deliver flexible structures such as blood vessel or bronchus closer to the heart or further away from the heart for safety during more minimal invasive surgeries, or radiographic procedures or tumor procedures such as ablation, cryotherapy, and the like.

The one or more attachments 14 may also be voice activated so that, when the surgeon is using his hands to operate, voice activated controls, such as controls programmed in the central console 16, can be activated, for example, to move the operating table in a desired fashion (e.g., twist the table 5 degrees to the right). The operating room may have reference points or localizers to provide a frame of reference for the positon of the table 12 and or attachments 14 to allow for precise movements. In some embodiment, the surgeon can adjust positions of the table 12 and attachments 14 by interaction with a hologram, by visualization, or through virtual reality goggles 18 (FIG. 2). Because the user can see where a particular body part is, the user can determine where they want the body part to be moved, and the system can move the body part to the desired location. In one embodiment, the system may use navigation to instruct the movement of the table. The user may provide commands to move the table either mechanically, acoustically, or optically, for example. Still other methods for moving the table 12 and/or attachments 14 are envisioned.

The one or more attachments 14 may include retractors which may be individually controlled, mechanically controlled, or electro or pneumatically controlled in order to apply force the patient to cause the desired movement of the patient. The retractors 14 may be linked as part of the operating table 12 or separate attachment features. In one embodiment, the retractors are existing type retractor systems. In one embodiment, the attachments 14 are inflatable type systems. In one embodiment, the attachments 14 are ratcheting type systems. The attachments 14 may be linked as part of the operating table system or could be add-on/bolt-on features.

Patient Positioning

During surgery patients are often asleep. With regional anesthesia where the patient could actively be awake during the procedure, positioning the patient in various positions such as a sitting/standing/rotating position may allow the pathology to be more evident or may allow for movement of the body part closer to the surgical field. The one or more retractors 14 on the operating table 12, or an operating bed, can move the patient's body parts during surgery while the patient is under anesthesia. In one embodiment, the bed could be a hydrobed, pneumatic, or hydraulically/fluid controlled bed system which could also control the temperature, water bath, etc. The one or more retractors 14 may be used to move (e.g., push) specific patient body parts closer to the surgical field, to an operating robot, to an endoscope, or a surgical procedure. As previously discussed, the system may allow twisting, moment flexion, extension, and/or torsion of the patient's body. The system may also include or be linked to a surgical console (e.g., central console 16).

Robotic Movement

The robotic system 10 may incorporate multiple levels of controlled robotics for moving the operating table 12 and/or attachments 14. For instance, servo motors may be used to cause movement of some or all of the components of the system 10. Servo motors allow for very precise control and require either direct cable or direct linear attachments. Additionally, piezo crystals can be used for fine movements of the system components. Piezo crystals may be used to move components that only require a high output to move. The piezo crystals may also be wirelessly controlled to eliminate the need for bulky wires or cables. The piezo crystals could be attached to a tip of a robotic arm attachment (e.g., attachment 14) or as an additional add-on or function independently from the robotic arm where the piezo crystals could allow fine movement at the tip, controller, or end effector. The operation of the piezo crystals may be controlled using electrical/acoustic controls.

Hydraulics may be used for large strength and gross movements. Hydraulics are very effective for large bulk, strength, or movement of larger objects in the human body. Thus, hydraulic motors may be used to position of the operating table 12, or coupled to one or more attachments 14 for movement of relatively large objects such as bones, fracture fragments, the pelvis, or large bulky retractors. Therefore, the system 10 may incorporate multiple levels of control including: 1) gross movement with hydraulic motors, 2) precise control using servo motors, and 3) fine movement using piezo crystals. The different levels of control could be on one robotic system 10 or linked to multiple systems working in consortium off the same platform. Each level of control may be linked together via the central console 16. Artificial Intelligence may also link the controls based on practice or movement.

Additionally, one or more of the robotic arm attachments (e.g., attachment 14) can be configured to automatically return to a home position after a procedure or movement is performed so that the surgeon does not have to try to manually move the arm. This feature may be included within a single robotic system or multiple robotic systems.

Figure 3:
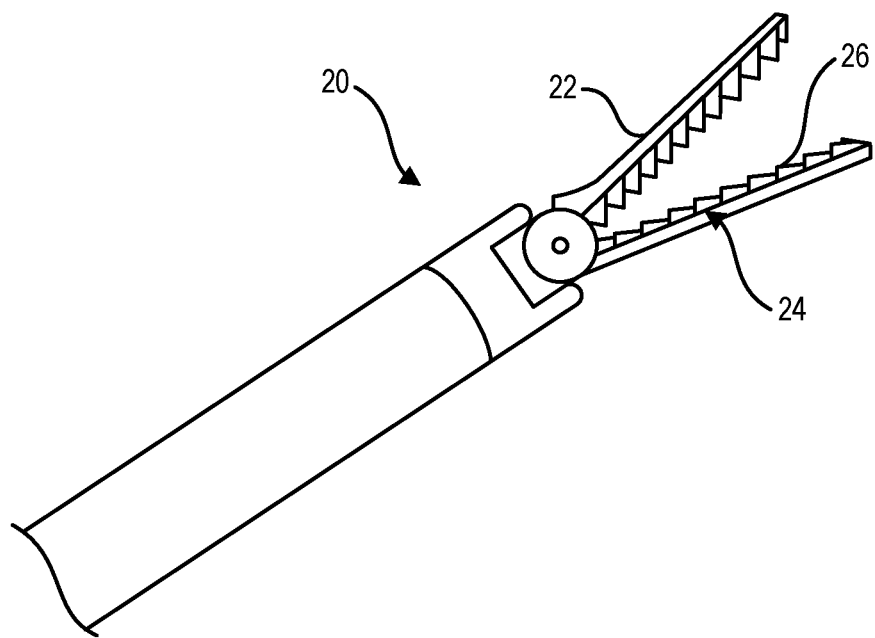
FIG. 3 is an illustration of a robotic arm.

Referring to FIG. 3, one or more robotic arms 20 may also include micro-ultrasound to allow for imaging at a portion of the robotic arm. For example, the micro-ultrasound may be integrated into a grasper 22 of the robotic arm. The miniaturization of ultrasound allows for imaging resolution similar to MRI (e.g., up to 30 µm) and operates in the frequency range of about 15 to about 80 MHz. By integrating micro-ultrasound into the robotic grasper 22 better intra-operative visualization of microstructures and vascular during robotic surgery can be achieved. In one embodiment, an array of micro-ultrasound pieces 24 can be embedded in one or both sides of a robotic grasper 22. Acoustically transparent material can also be used for the teeth 26 so that the grasper 22 functions normally. Turning on one or both of the arrays would give an image of the tissue held in the grasper. It is also considered with the miniaturization of optical coherence topography (OCT) hardware, the OCT hardware could be potentially integrated into a surgical manipulator or added through an additional surgical incision.

Multiple Robot Systems

Referring to FIGS. 1 and 2, a single screen or operator console, such as the central console 16, can be operated to control dual or multiple robots. Thus, a first robot may be operated to perform tasks at a first location on the body, and a second robot can be operated to perform tasks at a second location of the body. Additionally, the two or more robots may have different motion systems but because they are linked to the single console the operator can effect simultaneous operation of the robots. In one embodiment, manual control of robotic systems 10 (e.g. left/right handed control, foot control, or visual control) require different types of user interfaces. Thus, a user may control multiple robotic systems 10 through the same type of console approach so the systems can work in synchrony or unity. When the system is operating in synchrony mode, the robotic system 10 would determine which robots would need to move to accomplish the task at hand. In the current system, movement of the end effector of the robot is controlled by the surgeon, but the surgeon is not required to consider degrees of freedom that the robotic arm has. Using the same methods known in the art, such as matrix manipulation and linear algebra, to determine the robots' movement of articulating joints, the system could use a combination of one of multiple robots to accomplish the movement required by the surgeon without explicit instructions to both robots. Instead the surgeon would only be required to determine the desired movement of the end effector or visualization. Suitable technology for use with this system is disclosed in U.S. Ser. No. 10/287,379, filed Nov. 4, 2002; U.S. Ser. No. 16/113,666, filed Aug. 27, 2018; and U.S. Ser. No. 16/038,279, filed Jul. 18, 2018.

In one embodiment, a first robot of the robotic system 10 may be an adjustable robot configured to be guided through the digestive system either by magnetic or radiofrequency control, and a second robot of the robotic system could be a system such as the Intuitive da Vinvi robotic system (e.g. the single portal or standard Intuitive system), TransEnterix, MAKO, or other similar robotic systems. These robotic of the robotic system 10 may be introduced within the body endoscopically through an open incision while there is a separate robot in the digestive system, vascular system, or coming in from an opposite direction in the body. A user may operate both of these robots in synchrony even though they have different motion systems. The first robot may be servo motor driven and controlled through navigation and/or through direct visualization. The first robot could also be passive (i.e., fixed to the body), simply passively going through the digestive system, delivered on a cannula or through a location in the body. The second robot may be controlled through navigation electromagnetics, optical, direct line of sight, radiofrequency, magnetics, or non-direct line of sight. The robots may also be controlled by other means without departing from the scope of the disclosure. Both the robots and control systems can use known surgical navigation methods, but other embodiments could use ultra-wideband (UWB) technology to precisely determine distance and location between components of the robotic system 10.

Further, the robotic system 10 can deliver a neuromodulation device to the central nervous system. The deliver could be done using OCT. OCT could help visualize tissue, specifically, for example, nerves. By using OCT combined with robotic system 10, the surgeon has enhanced visualization to deliver, for example, a neuromodulation device to the central nervous system through cannula, needle, vascular guidance, etc. The OCT could also be used for diagnosis, repair, or treatment to deliver cells or coatings such as myelin to deliver electrical charges to this local tissue. By linking OCT to neuromodulation technology, for example, but also to other technology such as neuro link, where if one could visualize specific nerve fibers one could repair them, remove them, release them, or deliver pharmaceuticals and/or therapeutic tissue growth/tissue enhancement that would allow tissue to heal or enhance growth through growth factors. One could use some of the robotic systems we described as well.

In one embodiment, the first robot could be utilized to look inside the body. For example, in the popliteal artery behind the knee, and the second robot (e.g. MAKO) could be located outside the body on the knee joint itself. A user would be able to link the two robots through the central console 16. Thus, even though the robots are not in direct visualization, they communicate different types of information in the robotic system 10 including, but not limited to, navigation, MRI, PET scan, ultrasound, etc. Additionally, a tip (e.g., grasper 22) of either robot may have additional diagnostic functionalities such as ultrasound, OCT, ultrasonic probes, magnetic probes, etc. to guide either of the robots and/or to avoid certain positional systems.

In one embodiment, the multiple robot system can be operated for the purpose of vascular repair. In this embodiment, a user can operate the first robot be an intra-vascular or intra-intestinal robot that could maintain internal lumen, and operate the second robot as an external robot (i.e. Intuitive) repairing the anastomosis. The robots would be linked through the central console 16 so that the two robots work together. In particular, the first robot may be operated to maintain internal patency of the anastomosis, and the second may work externally on the anastomosis. In one embodiment, the first robot works internally on the anastomosis by heat light/adhesives. In one embodiment, the second robot works externally by suturing adhesives, sleeves, or by delivering a stent or graft to maintain patency while the first robot is preparing reconstruction (e.g. around aneurysm, around a tumor, or around abnormal growth).

In one embodiment, the multiple robot system can be operated for treatment of a subject's brain. In this embodiment, the first robot can be located intravascular for brain, stroke, guidance, etc. The second robot may come in from outside the brain through guidance systems for robotics to deliver the second robot to a specific location within the brain in order to repair certain sections or remove certain sections of the brain, vascular, etc. such as for strokes, tumors, or intracranial lesions.

In one embodiment, the multiple robot system can be operated for treatment of the subject's heart. For instance, the system can be used for cardiac ablation. In this embodiment, the first robot works externally to detect where arrhythmias may occur through electrical charges or where vascular challenge may be in smaller vessels. An external device can help guide the second robot through minimally invasive access to repair that vascular region or to stop electrical fibers to prevent the patient from having arrhythmias in the heart such as atrial-fibrillation.

Additionally, for the multiple robotic systems 10, one robot could be deglitch the platform, one robot could be mobile relative to the platform, and the console of the platform could control both of these and sync.

Additionally, the central console control 16 could be simultaneous like a drone versus a boat, such as disclosed in U.S. Ser. No. 16/113,666, filed Aug. 27, 2018. This disclosure can be used as a way to guide a position using things like Technetium 99 scans, etc.

Regarding multiple robotic system, robotic types, robotic drive mechanisms, robotic navigation system, and robotic stabilization platform should be considered. In accordance with the present disclosure, five types of robotics are typically utilized: a macro robot, a mini robot, a micro robot, a cellular robotic system, and a nano robotic system. For example, but not limiting to, the macro robot could be a traditional Stryker robot system such as a MAKO or ROSA. The macro robot is typically fixated to a floor or wall system. Alternatively, the mini robot may be positioned or stabilized to an operating table or to a smaller surface. The micro robot would be potentially stabilized to soft tissue and could be introduced by a separate robotic system or navigated to specific location. For example, the micro robot could be fixed to tissue, bone, or a vessel within the patient. Alternatively, the micro robot could also be ingested into the patient's GI tract and secondary used to locate. The cellular robotic system can be used to identify very small tissue and be able to reconstruct, repair, or stabilize at cell level. The cellular robot may, for example, be fastened with an adhesive or via Van der Waals forces, electrical charges, or magnetic charges to specific local tissues. The Nano robotic system would then be stabilized and/or positioned in a location with electromagnetic forces or motion forces.

Each of these robotic systems vary in terms of size and stability and in terms of what tissue and what types of reconstruction, repair, and procedures they aid. The robotic systems are positioned on different surfaces and in different locations. The robotic systems, such as the micro robot or nano robotic system could be ingestible, could be passively driven into position, or could be drive by radiofrequency, electromagnetic, or motion forces. The robotic systems could be driven by external magnets, for example, to a specific location in the digestive tract or in specific body. Alternatively, the robotic systems could also be positioned by a larger robotic system with position of a lower robotic system. These could also have degradable electronics as we previously mentioned in the patents incorporated by reference throughout this disclosure on biodegradables. The robotic systems could be coated by PLA/PGA or other degradable polymers. The robotic systems could be fibers, sensors, or any type of electronic component and could completely degrade inside the patient's body. These robotic systems, especially micro and Nano could be in part biodegradable systems where a metallic part may be biologic. As the biologic component, which is an insulator, is released, the robot no longer functions. This could also be used for sensor systems.

These robotic systems do not have to be simply for human use but as single robotic systems or in parallel they could be operated by the same platform or work in conjunction or series. For example, but not limiting to, the macro may position, the mini may remain stationary based and be stabilized to a specific smaller surface. The macro may be positioned to a body part or ingested and stabilized, and the cellular could be used to repair/reconstruct/move cells or tissues.

The robotics could be used also for medical or non-medical procedures. They could be Artificial Intelligence controlled as mentioned in reference by incorporation in prior Artificial Intelligence patent. One could learn over time where robotic system could be positioned, implanted, or placed and then link two together through Artificial Intelligence control. For example, macro DaVinci might be working with macro ingestible robot which may also be working with a mini robot attached to the operating table to move a body part to a specific location or how a table works and precisely control moving a body part specifically so it can be delivered to the appropriate position that a macro robot may want to use, e.g. DaVinci or MAKO, and deliver this to a specific location.

Consoles, for example the console 16, could link two, three, or multiple robots to function so macro, mini, micro, cellular, or nano robotic systems could work in tandem series or harmony with single console or single software system using Artificial Intelligence and/or navigation protocols to do this.

Operating Room Localization Systems

In combination with the robotic systems 10, the operating room can be equipped with GPS in order to tract the movement of objects within the operating room. For instance, GPS trackers 30, as shown in FIGS. 1 and 2, may be disposed throughout the operating room at fixed and/or known positions (e.g., non-bearing points in the ceiling, floor, etc.). The trackers 30 could be traditional satellite GPS receivers or a local tracking network could be made using UWB, optical, magnetic, radiofrequency, microwave, etc. One or more trackers 30 may be located on the operating table 12, robotics system(s) (e.g., attachments 14), the surgeon, the patient, and any other person in the operating room (e.g., anesthesiologist, nursing staff, etc.). Thus, the movement of all the individuals in the room can be tracked. Moreover, the precise movement of specific instruments held or operated by the individuals can be tracked. Therefore, the trackers 30 are localized with the robotic system to know where each individual is relative to locations in the room and relative to the operating table. In one embodiment, the trackers 30 are positioned on a netting (not shown) or other support structure around the room at specific pinpoint locations so the movement and location of the robot systems can be accurately monitored.

Additionally, if an MRI, PET scan, ultrasound, bone scan, etc. is taken in the operating room it can be mapped relative to the operating room based on the known dimensions of the operating room. It will be understood that the position information can be acquired within any room in which the size of the room and the position of the instruments is known. Thus, the mapping does not have to be specifically in the operating room but could be for example positioned distances off a wall or floor to give precise and reproducible locators relative to the room itself. Therefore, individuals in the room can work in synchrony and the positions and orientations of the operating table 12 and robotic systems 10 can be accurately tracked. This can be especially beneficial for mobile robotic systems such as systems that travel through the digestive system. The trackers 30 may also be placed on other medical devices such as catheters. Overall, the GPS system provides positional markers and GPS relative to known trackers in the room.

Additionally, the GPS system can be used to track the individuals in a room including their hand/fingers motion. In particular, a plurality of sensors (i.e., trackers 30) can be located in the fingertips of medical gloves 32 (FIG. 2) worn by the individuals so that the exact position of the individuals hands in the operating room are known. The system may also be able to track the position of the sensors around fixed objects if they are magnetic. For example, the system may use infrared or AI to track the sensor so that even though a device may get in the way the system could still extrapolate the location of the sensor. Tracking may also be done acoustically, through other types of mapping trackers, and via machine vision.

It will be understood that any number of trackers 30 may be used within a room. For example, there may be ten trackers 30 in the room. However, at a minimum, only three trackers 30 are needed to precisely localize where a finger is or an arm is relative to the table 12, or relative to the patient, or relative to robotic systems 10, or relative to surgical instrument, or relative to a tray of instruments, for example. This would limit or change motion patterns and eliminate unnecessary motion of support staff, scrub assistants, and even the surgeons themselves retraining the individuals in the room on how to improve efficiencies of the individuals and activities during a procedure.

Accordingly, the robot system (e.g., attachment 14) is linked to the operating room table 12. The system is also linked to the individuals in the room (e.g., surgeon, assistant, anesthetist). In one embodiment, an endotracheal tube can have trackers 30 for detecting movement patterns. The movements can then be linked to the robotic console 16 to advise either acoustically, manually, or through sensors on the gloves 32, scrubs, etc. to tell patients, assistants, or the operating room table 12 precisely where to move. This would allow movement of the operating room table 12 relative to where a surgeon wants the robotic system to move. For example, if the abdomen is neutral, the robotic system is in one position. If one torques the table ten degrees one direction, ten degrees another, flexes/extends the table, or allows rotation, then this would allow an individual to deliver the body part closer to where the robotic arm is rather than having to move the robotic arm to the body part. This can enhance the opportunities in surgery especially when patients are very obese. If a patient is very large, it is preferred to move the table 12 to the robotic system 10 and link these motion patterns.

The robotic and GPS systems allow for artificial intelligence to learn the patterns of how individuals move during surgical procedures. As such, the anesthetist, assistants, and other operating room attendants work with the surgeon and are linked together with sensors/wearables so that they can learn efficiencies and educate themselves on each other's movements during the surgical procedure. Ideally, individuals should move where equipment should be, retractors should be placed in their proper position, patients should be moved as needed for the procedure, and the correct type of anesthesia should be used. For example, if hypotensive, anesthesia or cardioplegia should be used to slow the heart down or change the respiratory pattern while work is being done in/around the lungs. Anesthetists work together with the surgeon and with the assistants so everyone knows where all the body parts are and how these are linked to the robots, endoscopes, or other surgical apparatus such as the operating table 12. These learned patterns could then be fixed to standardize the surgical procedure. To create a labeled data set of movement patterns to train an artificial intelligence system such as one using a convolutional neural network (CNN), the trackers for surgical staff could have all a unique code, which could be used in a training set for the CNN.

It has previously been discussed how various components could be linked to an operating room environment with a GPS tracker system. This facilitates everyone working together to perform a procedure as efficiently as possible learning how one person has developed these trends and translated into other operating rooms and other locations to decrease time, improve efficiencies, decrease infections, decrease complications, and also be able to do newer surgical procedures with smaller incisions and smaller approaches. This could be very useful for anesthesia techniques, surgical assistants, and scrub nurses who are conventionally not linked to the surgeon but rather are working on the console while the surgeon looking at the surgical site (e.g., patient/surgical tool) where the other staff cannot see what the surgeon sees. Additionally, a camera could be placed on an individual's glasses (e.g., virtual reality googles 18) or simply a wearable could allow them to guide specifically what the surgeon needs in addition to the entire team working as one unit. Also, the camera would aid in informing the surgeon or people operating how they should enhance their motion patterns to improve efficiency, time, etc. This could also be used to link different types of robotic systems.

It is also envisioned that external stimulus can be provided to prompt the individuals within the room regarding various actions during the procedure. For example, noxious stimuli either irritation, electrical pulse, electrical irritant, or thermal irritant can be provided. For instance, the stimuli could be provided so that an individual would be discouraged from changing a procedure to move into a specific pattern based on the noxious stimulus. The noxious stimulus could be a smell, thermal, electrical, chemical, electromagnetic, or a physical force. It could be applied by a wearable, gloves, an article of clothing, or microfibers. The stimulus could also be applied by an implantable. The stimulus may be linked to artificial intelligence to discourage the negative activity and reinforce the positive activity. The artificial intelligence creates new learning patterns for individuals/ assistants such as if someone changes during the surgical procedure and how they can catchup and work in unison with the individual. Thus, stimulus may be used for retraining purposes. These systems could be built into an entire suit, gloves, or body suit. It could also be with wearables on the patient's body. Thus, the noxious stimulus is used to retrain and then focus on artificial intelligence.

The stimuli also provides an opportunity to monitor how an individual responds to the stimuli. Additionally, feedback can be provided during the surgical procedure so that after the procedure or after the activity the individual can learn not just from the irritant or from the stimuli either positive or negative but then also visually reinforce this with cameras or navigation to allow the individual to change their motion pattern. For example, but not limiting to, for a fine motor activity of a baseball pitcher switching from one pitch to another to try to improve velocity, there can be a stimulus that reminds their muscle to fire or not to fire during certain patterns. To help change this, the individual can then watch these motion patterns via holograms and/or watch them via cameras which are following the patient at the same time to try to relearn using additional tools instead of just visual patterns or auditory patterns. The stimuli may be noxious or positive stimuli patterns. This, positive reinforcement can be incorporated as the proper movements and techniques are utilized. This could be done for numerous activities that require fine motor or gross motor control such as running or jumping. In one embodiment, positive reinforcement can be use in a surgical procedure. Through this stimuli, an assistant can be trained on how to move quickly and more efficiently during a surgical procedure.

Surgical Planning Software

Figure 4:
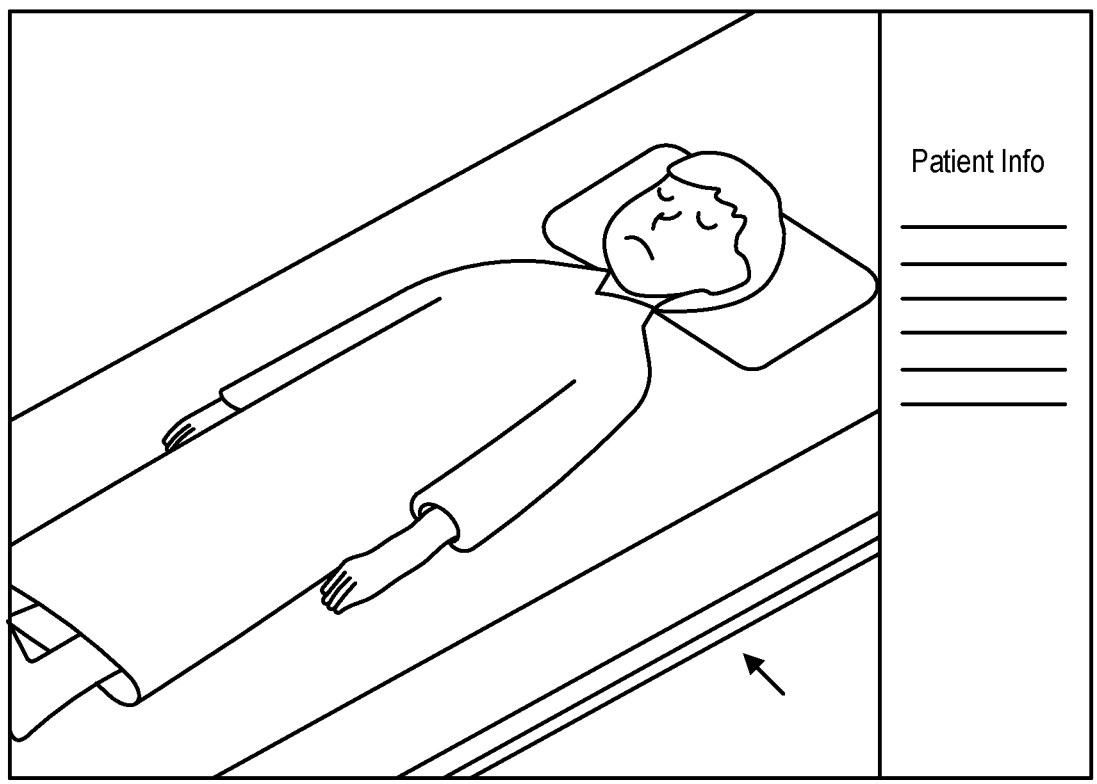
FIG. 4 is an illustration of an output of a surgical planning procedure.

Optimal patient position may be automatically calculated through software. Referring to FIG. 4, an exemplary picture of planning software shows the target surgery site on a kidney. However, the planning software is not limited to treatment on soft tissue, or a specific organ. When the surgeon is performing pre-operative planning or during a procedure, the surgeon may use a mouse, voice control, or other method to rotate the image for best access. The system will then calculate the best anatomical position for the surgery and the best position for the robotic system 10. In one embodiment, the position will show a recorded position guide for the surgery site to manually position the patient. In another embodiment, trackers on the patient, robot, and operating table 12 could be used to guide the staff and move the patient and equipment to the correct position. When everything is in the correct position, the user would receive a visual or audio feedback through a wearable. In another embodiment with active patient manipulators such a servos or hydraulic retractors, surgical bed, and other previously described embodiments, the planning software may automatically position the patient and the robotic system for optimal position (see FIG. 5).

Microbots

Microbots may also be used alone or as part of the robotics system and thus are configured to function completely independently. Microbots can be injected into the patient, swallowed by the patient, or placed in the vascular system of the patient. In one embodiment, the microbots are magnetically controlled. In another embodiment, the microbots are piezo controlled. The microbots may be passive, but the microbots have a working system. The microbots can be used for visualization, localization, or navigation. Additionally, the microbot may emit a signal so that, for instance, if the microbots are in the digestive system or vascular system, their position can be detected. The microbots may be sufficiently small such that they are configured to be passively moved around via blood flow, body flow, movement flow, or by pushing from the operating table. Thus, the microbots could be located within an important structure and give localization control so that standard robotic surgical procedures could be performed knowing exactly where the vascular supply is and/or the state of the vascular supply. For instance, the microbots can indicate a disrupted or moved vascular supply relative to the operating table, surgical robot, patient, assistant, etc. The microbots may be freely floated or magnetically controlled for example in a specific location in the body. The microbots can then attach themselves to the lumen of the vessel or to a specific area of the body and give localization or possibly small functional movement and then be released after the procedure is over, or move to another spot during the surgical procedure. Microbots could attach themselves to local tissue control through, for example, but not limiting to, friction, pneumatic, or charges. For example, the microbots could use flex polymer as a moment arm where a flex polymer charge is applied and certain polymers can flex or extend to lock into a desired position. The microbots are therefore actively controllable to control the microbots' ability to grasp tissue, hold tissue, or move to a specific location.

The microbots may also have fine motor control, wireless control, and/or magnetic guidance as well as fluid guidance and motion guidance for controlling the movement of the microbots. The microbots could flex/bend. These microbots may have small indentures to grasp the tissue. Control of the microbots allows for the selective grasp and release of tissue as needed for the particular procedure. The microbots may also have a friction that could be removed or they could float freely. During a procedure, the microbots can give diagnostic and/or potential therapeutic treatment input. For instance, microbots can be located on the inside the lumen of a tubular structure such as the intestine to provide the necessary treatment. When the robotic system is repairing the outer lumen, the microbots can maintain the inner lumen or help seal the inner lumen and deliver adhesive, cautery, sealant, for example, in small localized aliquots to the specific location while the outer tissue is being healed or repaired in a macro fashion (i.e. sutures, staples, etc.). The microbots thus maintain the inner lumen and seal the inner lumen preventing bacteria or fluid from flowing outside that space. Additionally or alternatively, the microbots could inflate to seal that space during the procedure so that bacteria, blood, or fluid would not leak out into the peroneal space or to the vascular space sealing off blood vessels. This process may be done temporarily by pneumatic balloon or via adhesives, coagulation, devices, etc. to seal off the desired space. Alternatively, the microbots could be used to deliver cells under a scaffold, place tissues on cells, place pharmacologic agents or deposit agents. In addition, the mircobots could be used to add Human-Pose Estimation or to allow one to use Artificial Intelligence to help guide and/or visualize the robotic system's function or activity.

Augmented Surgical Vision

It is also provided in this disclosure the capability of enhancing surgical vision such as endoscopic vision or open vision with machine vision. In one embodiment, goggles (e.g., goggles 18) are provided with a camera that can be worn by the surgeon. The googles can include single, dual, or multiple cameras. Thus, rather than looking through magnifying lenses, the surgeon can look through cameras and these cameras could be pointed to a specific location by the surgeon's direction. Alternatively, the cameras can direct the surgeon's attention to a specific location. For example, if a microbot is located inside the body or navigation inside the body and the surgeon is looking exactly where the area of tissue damage is, foreign body, or where the loosening is, structures inside the body may have navigation whether electromagnetic, radiofrequency, or ultrasound whether some localized or inside the body. The cameras are then configured to prompt the surgeon to pivot or move the surgeon's eyes (i.e. cameras or body) to the intended surgical spot and focus the site of the cameras on that depth of vision with the understanding of how far away the surgeon is from the surgical spot (e.g., 6 inches, 1 foot, or 2 feet). Rather than wearing microscopic lenses, which have fixed focal lengths, the cameras adjust automatically to give the surgeon a better position or location. The googles may also have Doppler radar to illuminate movement artifacts, to mitigate any motion sickness that may be caused by the cameras. Thus, the Doppler radar corrects for this and provides feedback. Additionally, fluoroscopic guidance, internal microbots, or other localizers or navigation can be used.

The surgical vision system may also be built through MRI, OCT, ultrasound, or other diagnostics and linked into the camera lenses to instruct or guide the surgeon to focus on exactly the right correction. Thus, the system could direct the surgeon's vision to where the pathology is and where they should be working. The surgical vision system may also be linked to the other components in the room (i.e., robotic system, individuals, etc.) thus providing other components and individuals with the vision features. This would aid, for example, in positioning where a retractor 14 should be located, how a patient should be moved, where a medical component or tool should be located, or how tissue should be grasped, removed, released, or repaired allowing the robotic system to move more accurately and efficiently. The individual would wear these machine vision camera lenses (possibly dual lenses or even triple lenses where the third would be localized to give depth, focal length, adjustment, and/or Doppler to compensate for motion patterns and allow the individual to focus on the surgical spot).

Connected Surgical Room

Figure 6:
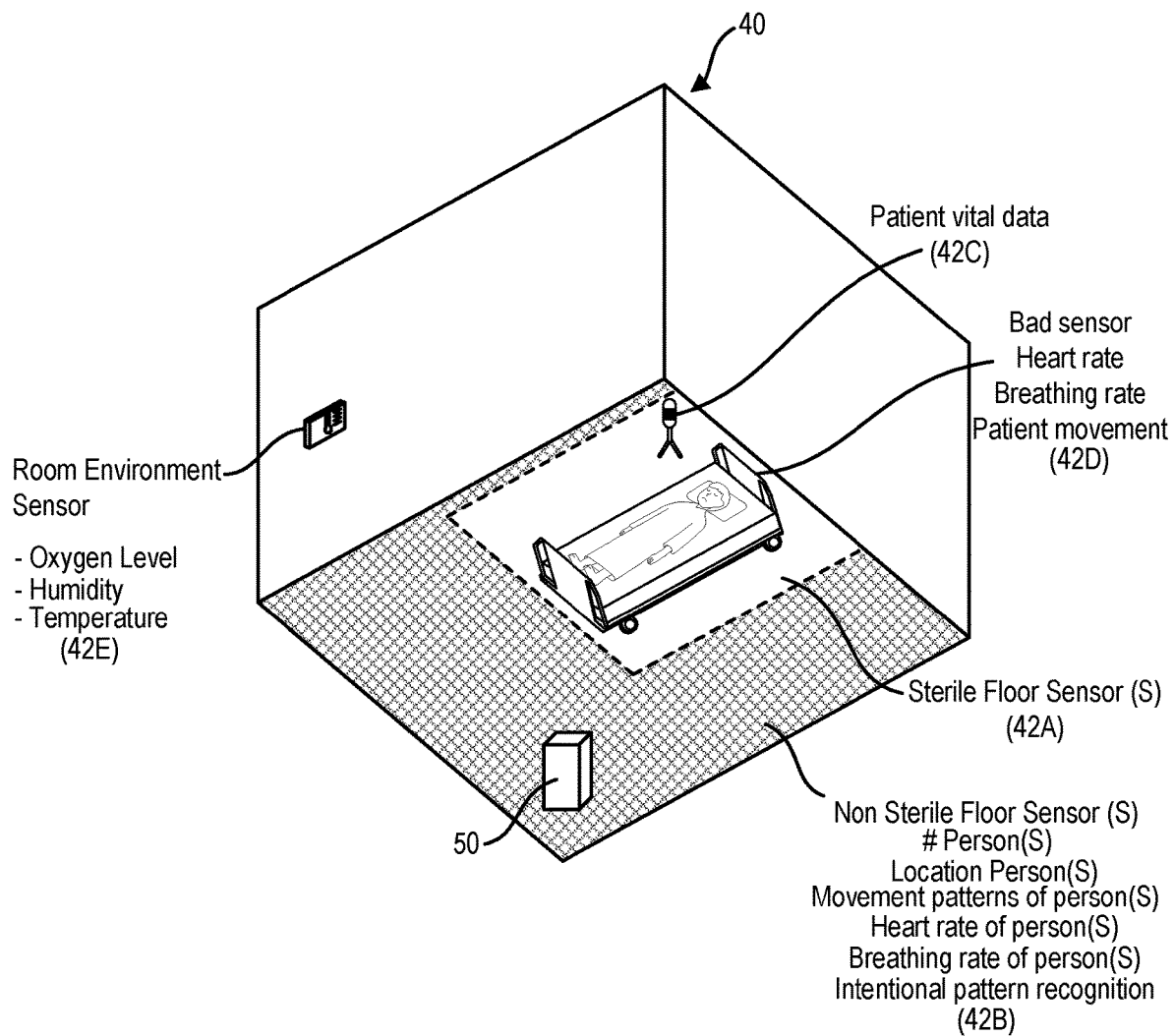
FIG. 6 is an illustration of a connected surgical room.
Figure 7:
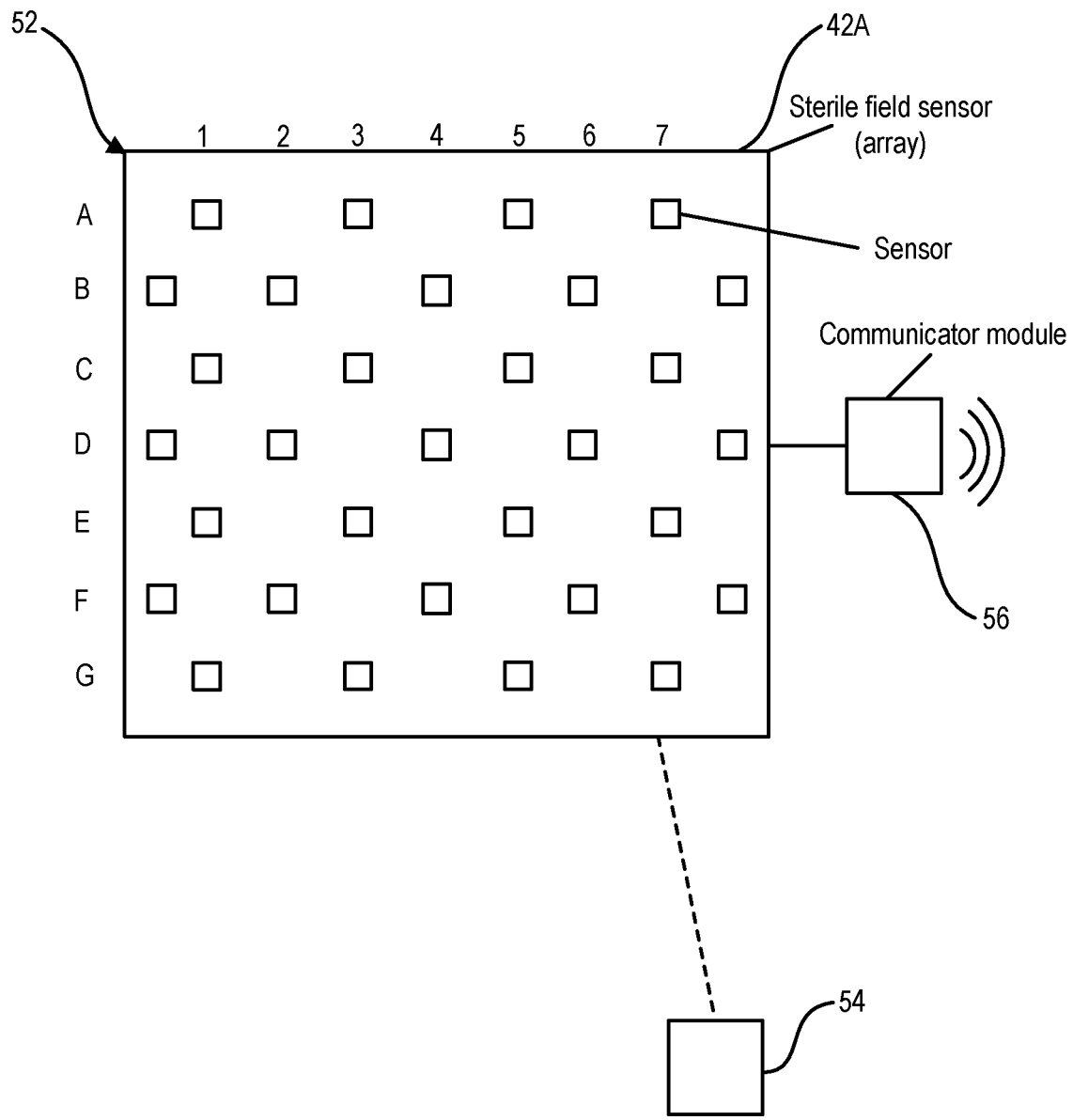
FIG. 7 is an illustration of a sensor pad.
Figure 8:
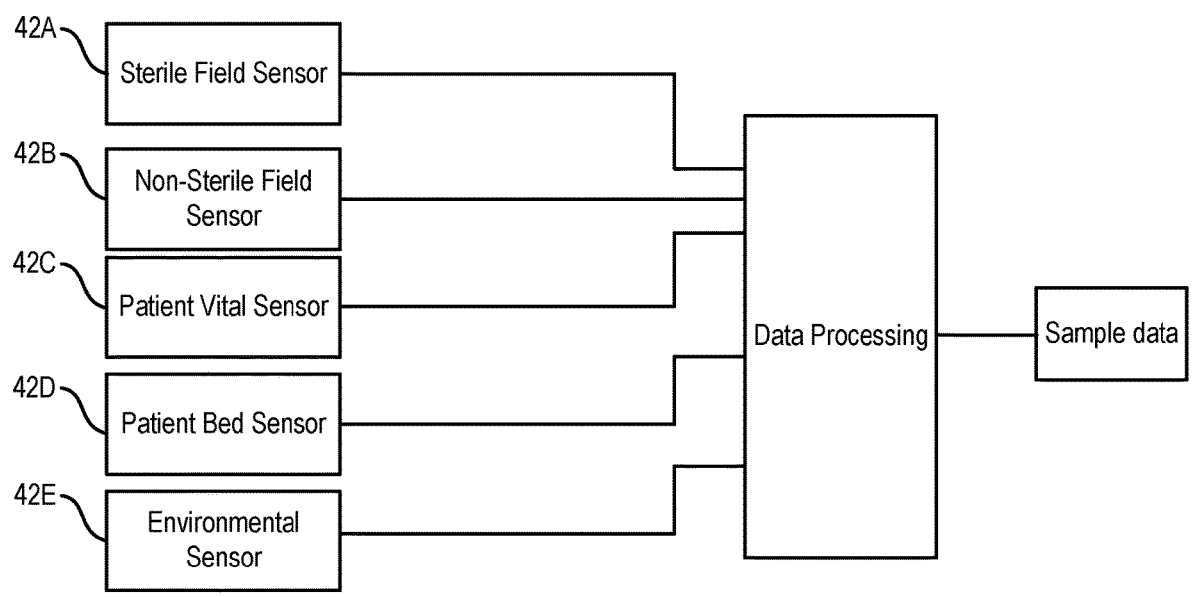
FIG. 8 is a schematic illustration of sensors in the connected surgical room.

Referring to FIG. 6, a connected surgical room is generally indicated at 40. The surgical room includes sensors 42 integrated throughout the room configured for measuring various parameters within the room including patient vitals, environmental conditions, personnel movement patterns and a number of personnel to determine optimal surgical room standards for improving patient surgical outcomes. As best shown in FIGS. 6-8, the sensors 42 are operatively connected to a data module to transmit the measured data to the data module for collection in real-time. In accordance with the present disclosure, the data module could be the central console 16. The real-time data can then be analyzed and processed into a performance report (FIG. 9). Once analyzed, the real-time data can be compressed to control storage space.

The connected surgical room 40 may comprise one or more of a sterile field floor sensor 42A, a non-sterile field floor sensor 42B, a patient vital monitor 42C, a patient bed monitor 42D, an environmental sensor 42E, and data module 50, as best shown in FIGS. 6 and 8. The data module 50 may compile the data from the sensor 42 and produce a surgical room performance report (FIG. 9). Other sensors may also be included without departing from the scope of the disclosure.

Sterile Floor Sensor

Referring to FIGS. 6 and 7, the sterile floor sensor(s) 42A may comprise a single sensor or an array of sensors that are integrated into flooring of the surgical room 40. In one embodiment, the sterile floor sensors 42A comprise an array of force sensors for detecting the pressure exerted on the floor by the individuals in the surgical room 40. The floor sensors 42A may be arranged on a force pad 52, as shown in FIG. 7. The force sensors 42A may be arranged within the surgical room 40 to enable location tracking of personnel movement throughout the room. The sensors 42A may also be operatively connected to a timer 54 so as to be able to determine time changes in the force patterns to track the weight, posture, and/or fatigue patterns of personnel. In addition, capacitive, proximity and other known sensors may be used alone or in conjunction with the force sensors 42A. The data from the floor sensors 42A can be sent wired or wirelessly to the data module.

In addition to just monitoring movement within the room 40, the force data measured by the sterile floor sensors 42A can be communicated between assisting personnel and physicians (i.e., individuals using the robotic device) in the room via a transmitter 56. In particular, the force data can be displayed on a monitor (e.g., data module 50) within the room 40 and/or worn by an individual in the room. Therefore, without looking up from the robotic monitor the physician can receive a graphical view of the location and movement patterns of all the assisting personnel. Using a double tap feature on the floor sensor 42A, the assisting personnel could indicate to the physician operating the robotic device, when a task is completed (e.g., robotic tool changed). The double tap feature could also provide a tactile or visual feedback to the physician controlling the robotic device. Thus, the physician could indicate to assisting personnel when a task is completed or to be performed by sending a tactile vibration to the assisting personnel standing on the sensor pad, as best shown in FIG. 7. In one embodiment machine vision could be used instead or pressure sensors. The availability of other surgical staff could be displayed using an augmented reality as icons or avatars in the peripheral vision of the surgeon depending on position.

In one embodiment, personnel data is pre-calibrated into the system to allow for tracking of each personnel based on weight and posture patterns. This would allow for the identity of each assisting personnel to be included in the data report.

In another embodiment, the sterile floor sensor 42A may comprise an imaging sensor configured to identify and track movement of personnel within the room 40. The imaging sensor 42A may comprise a single stationary camera or multiple stationary cameras placed throughout the room 40. In addition to tracking movement and number of personnel, the imaging processor may identify time duration changes in posture to identify fatigue in the individuals in the room 40.

Non-Sterile Floor Sensor

Referring to FIG. 6, the one or more non-sterile floor sensors 42B may comprise a single sensor or an array of sensors that are integrated into the flooring. In one embodiment, the sensors 42B are an array of force sensors. The force sensors 42B may be arranged to enable location tracking of personnel movement throughout the room 40. The sensors 42B can also determine time duration changes in force patterns to track weight, posture and fatigue patterns of personnel in the room 40. In addition, capacitive, proximity and other known sensors may be used alone or in conjunction with the force sensors 42B. The data from the sensors 42B will be sent wired or wirelessly to the data module.

In addition to just monitoring movement with the room 40, the force data measured by the non-sterile floor sensors 42B can be communicated between assisting personnel and physicians (i.e., individuals using the robotic device) in the room. In particular, the force data can be displayed on a monitor within the room and/or worn by an individual in the room. Therefore, without looking up from the robotic monitor the physician can receive a graphical view of the location and movement patterns of all the assisting personnel. Using a double tap feature on the floor sensor 42B, the assisting personnel could indicate to the physician operating the robotic device, when a task is completed (e.g., robotic tool changed). The double tap feature could also provide a tactile or visual feedback to the physician controlling the robotic device. Thus, the physician could indicate to assisting personnel when a task is completed or to be performed by sending a tactile vibration to the assisting personnel standing on the sensors 42B.

In one embodiment, the non-sterile floor sensor 42B may comprise an imaging sensor configured to identify and track movement of personnel within the room 40. The imaging sensor 42B may comprise a single stationary camera or multiple stationary cameras placed throughout the room 40. In addition to tracking movement and the number of personnel, the imaging processor would identify time duration changes in posture to identify fatigue in the individuals in the room 40.

Patient Vital Monitor

Patient vital monitors are generally known in the art. One example of an existing patient monitor technology is the Welch Patient Monitor described in U.S. Pat. No. 6,544,173—Patient Monitoring System. The present disclosure provides a patient vital monitor 42C which incorporates a standardized data protocol to transmit the vital data to the data module 50. In one embodiment, a visual sensor comprising a single camera or multiple cameras is placed throughout the surgical room 40. The visual sensors scan the room to find the location of the patient monitor display in the room. The visual sensor then focuses onto the display to read the patient vital data from the display. The vital data can then be transmitted to the data module 50 using wired or wireless communication.

Additionally or alternatively, the patient vital data can be sent to the robotic system monitor (e.g., central console 16) to allow the physician to monitor the patient's vitals without looking away from the robotic system 10 or having the assisting personnel vocally report the vitals. The robotic system 10 may also use visual or tactile alerts to inform the physician of vitals outside a preset limit.

Patient Bed Monitor

Patient bed monitors are generally known in the art. One example of an existing patient bed monitor technology is described by Bosch Gmbh in U.S. Pat. No. 9,820,658—Systems and Methods for Providing Interoperability Among Healthcare Devices. The present disclosure provides a patent bed monitor 42D that incorporates standardized data protocol to transmit the vital data measured by the bed to the data module 50. In one embodiment, a visual sensor comprises a single camera or multiple cameras of the same or different visual technologies. For example, a camera specifically calibrated for detecting minute movement may be used in conjunction with a thermal camera. These visual sensors would be placed throughout the surgical room 40. The visual sensor could then focus onto the patient to monitor the patient's minute movements and thermal response. As a result, the patent bed monitor 42D could determine various patient parameters including the patient's breathing rate, activity level, skin temperature, etc. The patient data could be transmitted to the data module 50 using wired or wireless communication.

The patient data could also be sent to the robotic system monitor (e.g., central console 16) to allow the physician to monitor the patient data without looking away from the robotic system 10 or having the assisting personnel vocally report the vitals. The robotic system 10 could use visual or tactile alerts to inform the physician of patient movement or body temperatures outside a preset limit.

Environment Sensor

Environment sensors are generally known in the art. One example of an existing environment sensor is the thermostats technology described by NEST in U.S. Pat. No. 9,234,668—User-Friendly, Network Connected Learning Thermostat and Related Systems and Methods. The present disclosure provides an environment sensor 42E that incorporates a standardized data protocol to transmit the environmental data measured by the thermostat to the data module 50.

Data Module

The data module 50 is comprised of a wired or wireless receiver. The data is received and processed using a standardized protocol. This standardized protocol allows for the data from each system to be compiled into single data points per specified sample rate. Upon receiving multiple data under a single sample point for an individual sensor, the multiple points will be averaged and the averaged data will be reported as the sample.

Performance Report

Referring to FIG. 9, the performance report will analyze the data for several factors including movement patterns for each assisting personnel and physician, patient vitals and movement throughout the entire procedure, and environmental conditions of the operating room throughout the entire procedure. Process indicators may be highlighted showing possible areas of improvement based on known successful or failed outcomes from previous procedure database (e.g., operating room temperatures near limits, humidity levels near limits, patient skin temp near limits, fatigued assisting personal, fatigued physician, assisting personnel number (too many or too few), and delayed assigning personnel response).

Additional Concept

The double-tap feature could be integrated into the robotic arm 20. When the assisting personnel has completed an assigned task the assisted personnel could double tap the robotic arm 20 which would send an alert to the robotic monitor for the physician to see.

Biometric Encryption Software

Figure 24:
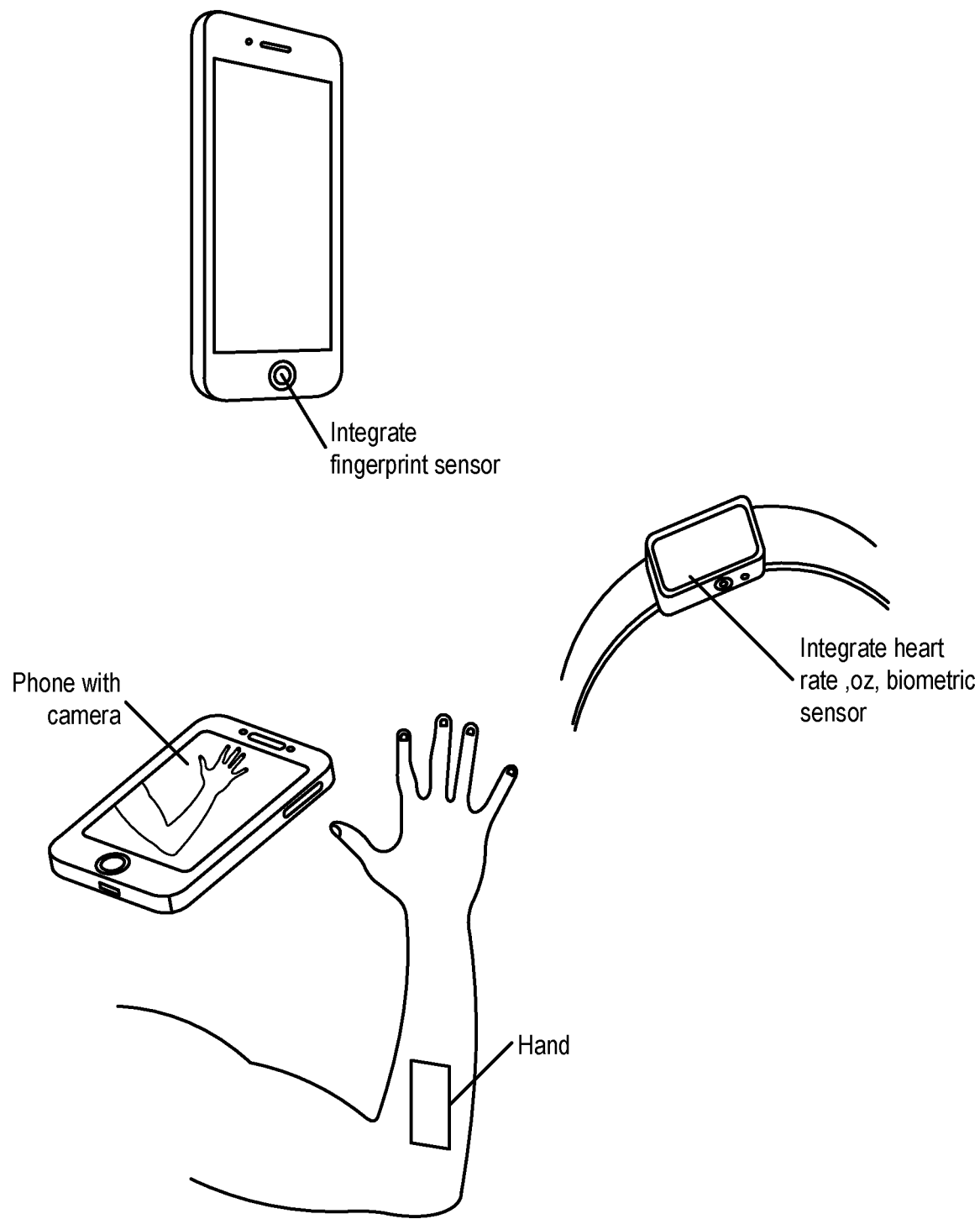
FIG. 24 an illustration of biometric encryption software being utilized for patient security.

The present disclosure also provides security for encryption technology, as best shown in FIG. 24. Encryption is a process that encodes a message or file so that it can only be read by select individuals. Encryption uses an algorithm to scramble, or encrypt, data and then uses a key for the receiving party to unscramble, or decrypt, the information. In the present security system, encrypted data is opened using keys based on patient's physical attributes. The physical attributes can be rectal scans or finger prints. Alternatively, other areas of the body could be used such as different surfaces of the body (i.e., skin, moles, scars, skin patterns on specific portions of someone's body such as the back of the hand, the back of the neck, or face). In specific locations, the scan could be performed over the surface of the body, or a laser could be used to look at the depth of the skin and depth of the tissue. As the profile and characteristics of the body features may change over time as the individual ages, this allows a different way not only to help for dermatologic applications but for diagnosis/disease with change in aging patterns. Also these topical issues could be the keys that are used to encrypt technology for the sender and receiver. For example, a camera for the computer, smartphone, or the like may localize in the body. An additional light may also localize in the body. Additionally, a motion sensor may be localized in the body to detect motion pattern. The body surface could be specific location such as 1 centimeter on the front of the thigh or 1 centimeter on the back of the hand. The body surface could have surface typography which could be 3-dimensional. The body surface could be on the index finger or back of the second finger. The location of the body scan may change over time. For example, one day the location of the scan may be on the finger and the next day it could be by the elbow or a different location. Additionally, multiple locations can be scanned and linked up. This allows parcels of information to be delivered so that one large e-mail or one packet of information can be sent where one person could open one portion of the packet and another person could open another portion based on their respective key (i.e., specific body/physical attributes). This could also be done via scans. For example, ultrasound may be used to scan the surface of the tissue and also scan internal organs to see tissue types, movement patterns, thickness, fat, and other internal characteristics. In one embodiment, the ultrasound is located on a computer or phone. An ultrasound can perform a scanning method and be placed on encryption based technology so it scans a certain portion of the body that would be known, such as the elbow, to look at the tissue patterns, thickness of the tissue, location, portion of the face, facial structures, etc. The 3-dimensional scan could then be linked to help with encryption. The scan location could be moved on a daily basis to a specific location of the body. For example, one day it might be the left cheek just underneath the eye to specific location and then the next day it may be placed along the neck or the back of the hand or other locations to ensure encryption safety. Creases on the skin or moles that change pattern over time can also be used. The thermal gradient may also be linked to the skin patterns. Additionally, ultrasound depth patterns may be linked. Machine vision and/or cameras can be used to scan very close so that scan magnifications of 1×, 3×, 5× can be acquired depending on how the patterns look to ensure encryption and can also be used as a new key. This allows scans for dermatologic or lesions which can be done using a smartphone with combinations of skin and ultrasound and/or potential electrical and/or camera motion qualities. Therefore, the encryption process can be used for diagnostic categories and link into MRI, x-rays, and other diagnostics, and be used to evaluate patient care by scanning an individual's body to monitor changes over time. The scanning can be performed with a smartphone linked to MRI or other diagnostics.

Diagnostics on Tissue Vibrating Frequency

Figure 23:
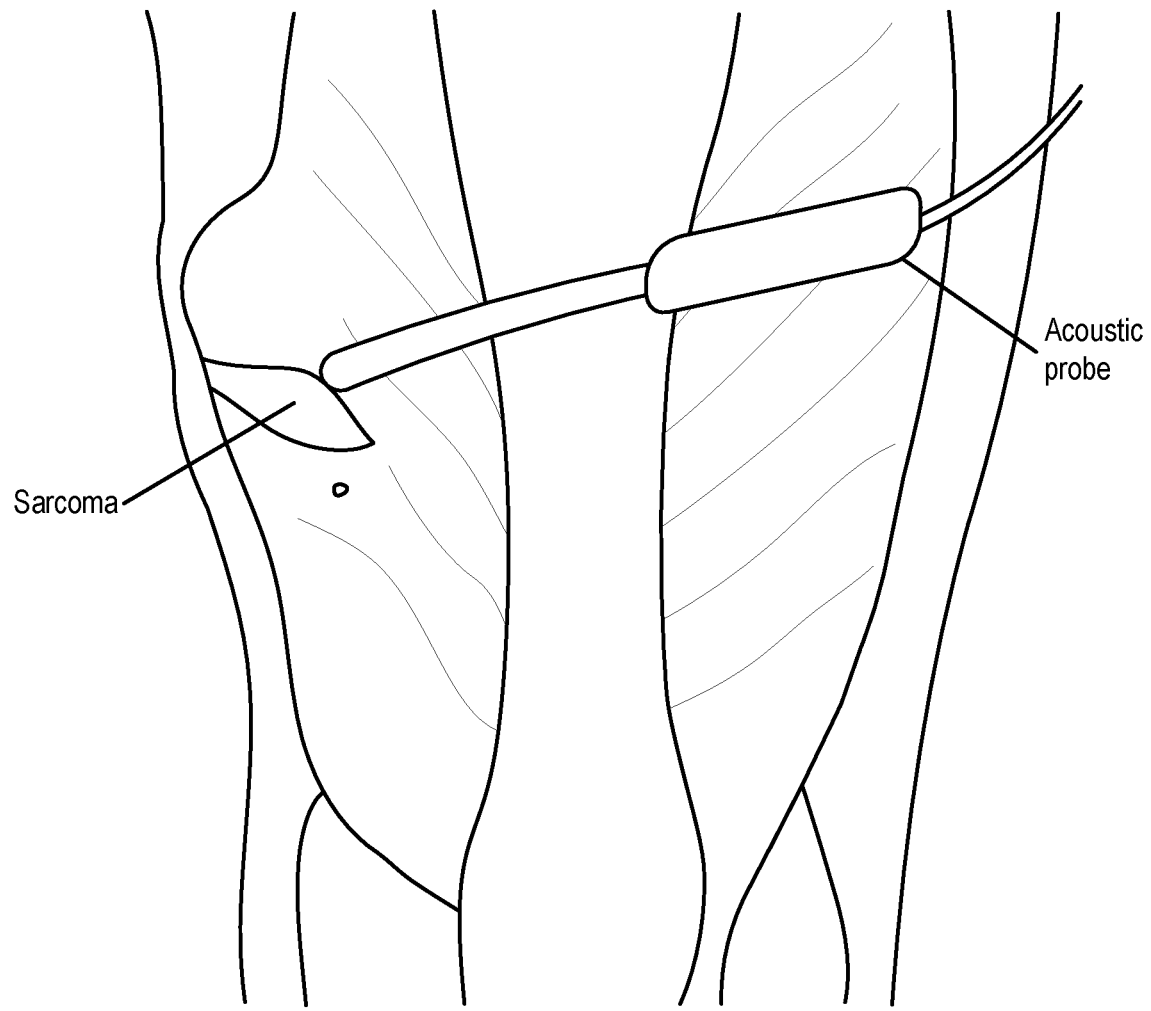
FIG. 23 is an illustration of a diagnosis of tissue vibrating frequency.

The present disclosure also provides for identifying abnormal tissue, tumor tissue, abnormally reacting tissue (i.e. hyperplasia), and the like, as best shown in FIG. 23. For example, tissue that will be identified is tissue that is reproducing rapidly has increased blood flow to the area. However, cells within the tissues themselves have more nuclei and tend to be denser than normal tissue that has normal collagen scaffold and vascular supplies. These tumor cells also multiply more quickly. These abnormal cells could be diagnosed with fluorescents and through injected labeling technologies. Also, at a local or microscopic level, the tissue can be vibrated such as acoustically or ultrasonically. If the tissue is firm, well fixed, attaching or denser, it will have a different vibrating frequency than the other tissue. Thus, by measuring the vibration frequency, the abnormal cells can be identified for removal if necessary. This could also be done on a diagnostic basis combining this with ultrasound, MRI, or PET scan. Additionally or alternatively, thermal energy may be used to heat the local tissue (e.g., by a few degrees) to see if the change in temperature changes the density or signal of the MRI. This can be done locally or regionally. For example, the entire MRI chamber may be heated, or the tissue itself may be heated locally. This local heating could occur with ultrasound, microwaves, ESWT therapy, or the like. Once this tissue is heated, a MRI or PET scan may have a different signal intensity which can be observed and used to diagnose the abnormal cells. The heating may also be performed acoustically or through vibration. In one embodiment, the process is performed on a diagnostic platform (i.e. MRI, PET scan, etc.). The process can be done during surgery when a surgeon is locating these small clusters or denser or more adherent tissue which tend to be more malignant in nature and the tissue can then be removed.

In addition to the vibratory and thermal identification methods, abnormal tissue can be identified using electrical signals. Tissues that are more rapidly multiplying are also ingesting more food, nutrients, and therefore have different electrical conductivity. Thus, single or combination ports can be used to identify abnormal tissue, infected tissue, or tumor tissue and then how to treat those tissues by removal either on a micro or macro level.

It is also provided that tissue within the body can be stressed to determine points for modification and underdiagnose the circumstances. The tissue may be stressed in a variety of ways. For example, the tissue may be stressed by direct compression. The compression can be accomplished either pneumatically, mechanically, and/or by other stress method such as thermal, acoustic, and the like. The compression may be performed at the "magic angle" (i.e. about 55 degrees). Tissues that are dense are less likely to flatten out or move. The internal fluid may function as barriers. Through the compression process, different tissue planes, different tissues lines, and abnormal tissue patterns may be identified. Bodies are static on MRI or PET scan or even radiographs. By moving the bodies, it provides a better chance to identify abnormal or diseased tissue.

Myelin—Insulated Conductors

The subject matter described herein relates to insulated conductors and, more particularly, to insulated conductors including a biologically active material. Examples of the disclosure include an electrical conductor and an insulator coupled to the electrical conductor such that the insulator at least partially insulates the electrical conductor. Examples described herein include biologic, biocompatible, and/or biodegradable materials. The insulator, for example, may include myelin or a myelin-like material. Myelin or myelin-like materials may be harvested, synthesized, and/or cultured to develop biocompatible insulators.

Figure 10:
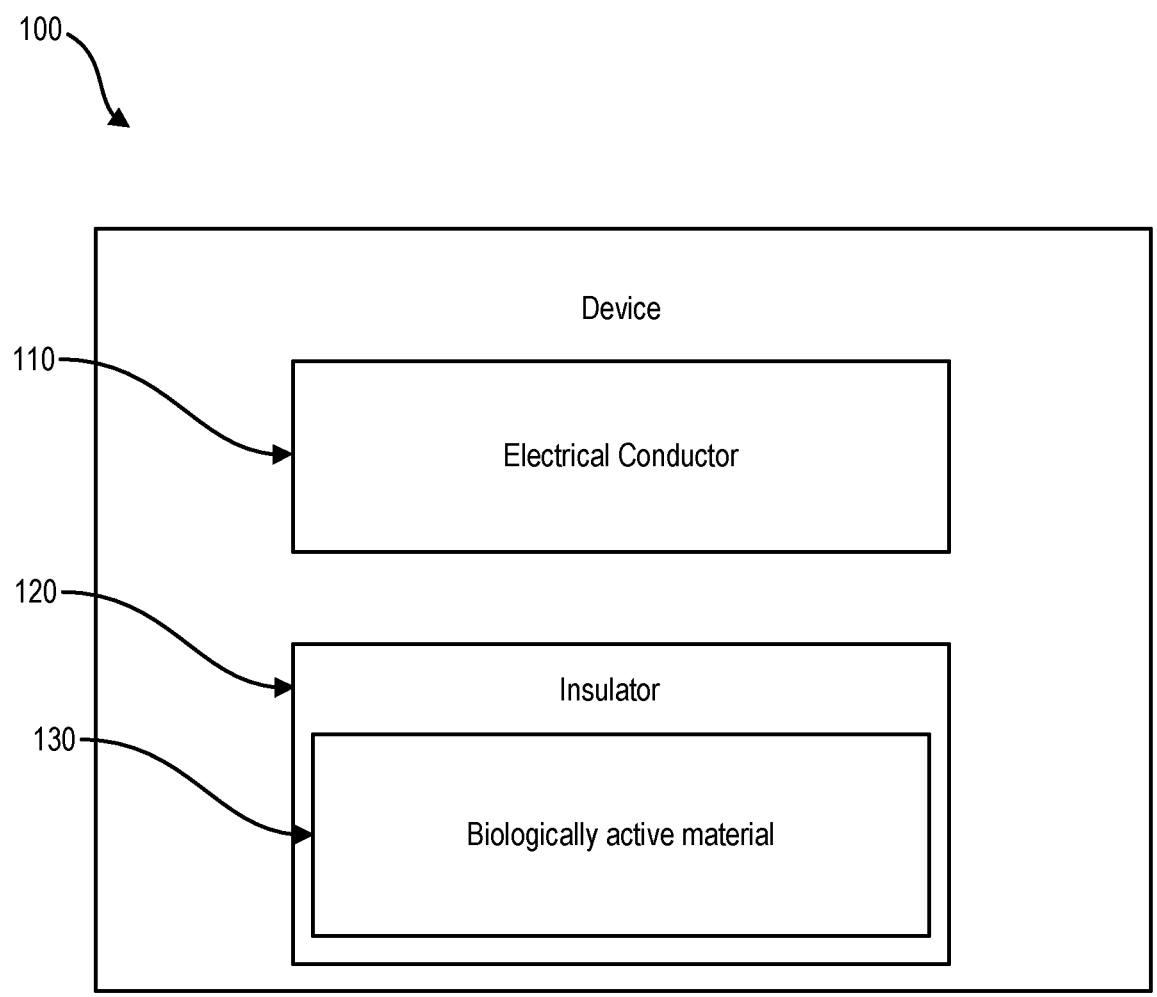
FIG. 10 is a block diagram of an example implantable device including an electrical conductor and a biologically active insulator.

FIG. 10 shows an example implantable device 100. The implantable device 100 may be implanted or inserted in a living organism (e.g., humans, animals, etc.), for example, using an imaging system (e.g., magnetic resonance imaging (MRI), x-ray imaging, ultrasound imaging, etc.) and/or a syringe or other injection system. In one example, the implantable device 100 may be implanted using a robotic system, which may include any of the robotic systems described above herein.

The implantable device 100 includes an electrical conductor 110 that may be used to channel electricity to and/or from an electrode, a stimulator, an actuator, and/or a sensor. The electricity may be channeled, for example, to apply voltage, current, and/or power to a target. The electrical conductor 110 may be coupled to a power source (e.g., battery, electric motor), a communication device (e.g., transmitter, receiver, transceiver), and/or a scaffold or coil such that the implantable device 100 generates an electric field. Examples of scaffolds, which may be used in conjunction with this disclosure, are provided in U.S. Ser. No. 16/824,201, filed Mar. 19, 2020, the contents of which are incorporated by reference. In some examples, the implantable device 100 is used for wireless communication, which may be incorporated into a robotic system such as one described above herein. The electrical conductor 110 includes or is made from one or more electrically-conductive materials (e.g., platinum, iridium, rhodium, gold, tungsten, tantalum).

The implantable device 100 includes an insulator 120 that is coupleable to the electrical conductor 110 such that the insulator 120 at least partially electrically and/or thermally insulates the electrical conductor 110. The insulator 120 includes or is made of one or more biologically active materials 130. As defined herein, the term "biologically active material" refers to a material that is of biological origin, is derived from biological origin, or is a synthetically derived homolog to those of biological origin and/or to materials which may be acted upon by organisms to cause the modification and/or degradation of the materials on a chemical level.

The biologically active materials 130 may be or may include a polymer, a protein, myelin or a myelin-like material, and/or one or more cells. Additionally or alternatively, other biological containing or sourced materials or non-biological containing or sourced materials may be used in the insulator 120 described herein. The biologically active materials 130 may be substantially biologic (e.g., bacterial with non-pathological bacteria) or be substantially non-biologic (e.g., polymer). In some examples, the biologically active materials 130 are biodegradable. As described herein, the term "biodegradable" refers to being capable of decomposing in or being decomposed by a living organism. Examples of biodegradable polymers, which may be used in conjunction with this disclosure, are provided in U.S. Ser. No. 16/405,046, May 7, 2019, the contents of which are incorporated by reference.

Polymers may be obtained by any means known to those in the art. In some examples, the biologically active materials 130 are or include biologically sourced polymers or derivatives thereof. For example, the polymer may be or may include one or more polysaccharides (e.g., starches, starch derivatives, cellulose, cellulose derivatives, cellulose ethers). In some examples, the biologically active materials 130 are or include synthetic polymers, or derivatives or precursors thereof. For example, the polymer may be or may include one or more acrylic polymers, polyester, and/or copolymers.

Proteins may be obtained by any means known to those in the art. In some examples, the biologically active materials 130 are or include one or more proteins derived and/or extracted from a biomass. For example, the protein may be or may include a collagen or a collagen-like material, including type I collagen, type II collagen, type III collagen, type IV collagen, type V collagen, and/or other types of collagen or derivatives or precursors thereof. In some examples, the biologically active materials 130 are grown on a scaffold and/or form a scaffold for use in tissue engineering.

Myelin or myelin like material may be used to help increase a speed at which electrical impulses propagate along the electrical conductor 110 (e.g., via saltatory conduction). Myelin or myelin-like materials may be obtained by any means known to those in the art. In some examples, the biologically active materials 130 are or include myelin or myelin-like material harvested from a natural source, such as an organism (e.g. livestock, humans). Additionally or alternatively, the myelin and/or myelin-like material may be artificially cultured and/or synthetically formulated. The myelin or myelin-like material may be formed or grown into any shape. In some examples, the insulator 120 includes a plurality of myelin sheaths extending about the electrical conductor 110. Additionally or alternatively, the myelin and/or myelin-like material may be formed or grown into sheets, which may be employed directly or further shaped, and/or deposited or grown on a scaffold.

Cells may be obtained by any means known to those in the art. The cells may include dead cells and/or live cells. For example, the cells may be or may include one or more viable cells that stick to each other (e.g., biofilm). In some examples, the cells 640 include bacterial cells and/or mammalian cells, including human cells and/or stem cells. The cells may grow, reproduce, and/or differentiate such that the insulator 120 is configured to grow and/or repair itself. In some examples, one or more bacterial cells are selected from those which are nonpathogenic to humans. The cells may be grown on a three-dimensional scaffold.

The electrical conductor 110 and/or the insulator 120 may include or be made from one or more biocompatible materials. In some examples, the biocompatible materials may be ultrasonically bonded or adhered with adhesives on scaffold. In some examples, an exposed portion of the electrical conductor 110 (i.e., a portion of the electrical conductor 110 that is not covered by the insulator 120) is coated or plated with one or more biocompatible, electrically-conductive materials.

The electrical conductor 110 and/or insulator 120 may include or be made from one or more biodegradable materials. As described herein, "biodegradable" refers to being capable of decomposing in or decomposed by a living organism. For example, the electrical conductor 110 and/or insulator 120 may include one or more materials configured to degrade and resorb in a body of a living organism in 1 day to years. In some examples, the implantable device 100 is configured such that a conductance of the electrical conductor 110 decreases in vivo. A decrease in conductance may help control an end use effect of the implantable device 100 and/or electrical conductor 110 over time.

The electrical conductor 110 and/or insulator 120 may include or be made from one or more regenerative materials. The electrical conductor 110 and/or insulator 120 may include or contain, for example, live cells. In this manner, the implantable device 100, electrical conductor 110, and/or insulator 120 may be configured to heal itself. In some examples, the implantable device 100, electrical conductor 110, insulator 120, and/or biologically active material 130 is maintained in a cell culture prior to use.

Figure 11:
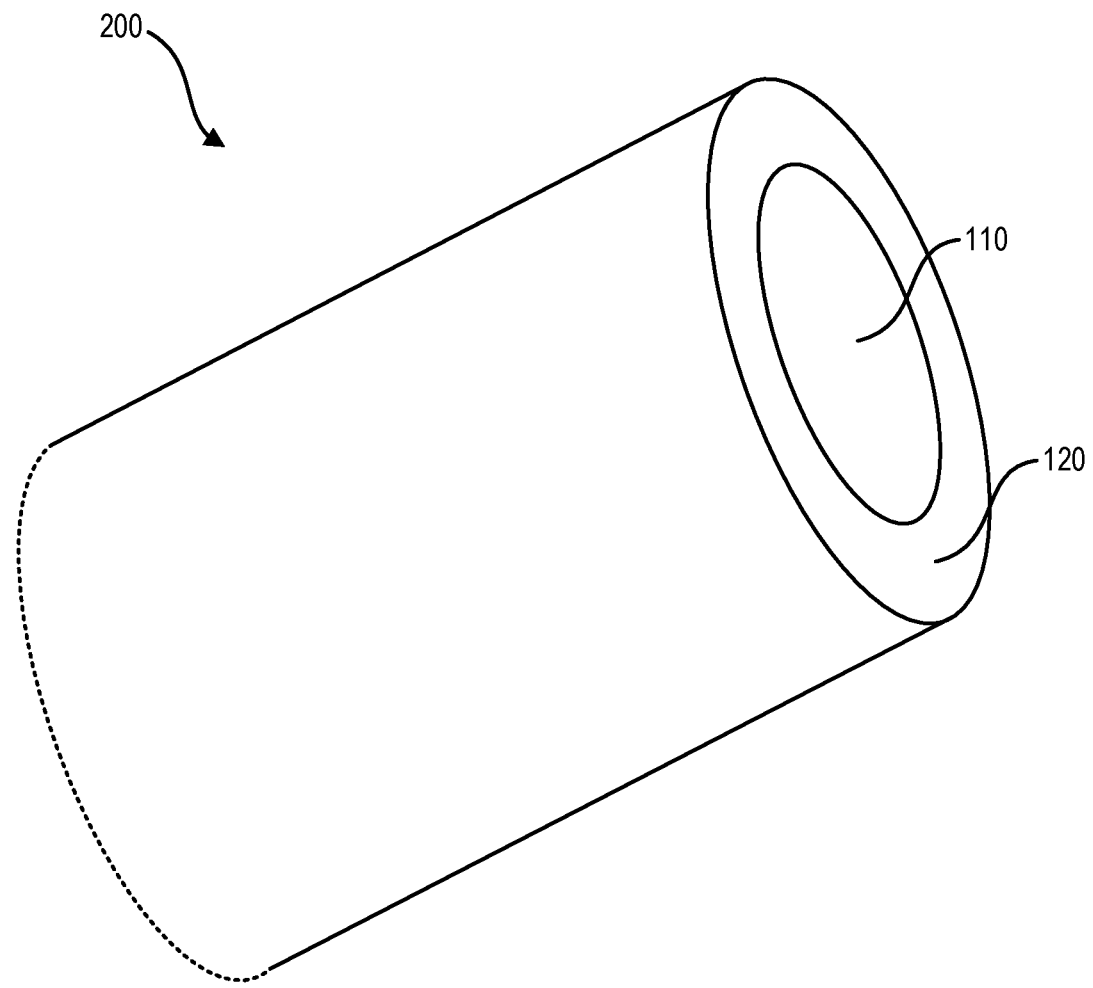
FIG. 11 is a partial cutaway view of an example wire.

FIG. 11 shows an example electrical wire 200 (e.g., implantable device 100) including an electrical conductor 110 and an insulator 120. As shown in FIG. 11, the insulator 120 may be in physical contact with and/or extend at least partially about the electrical conductor 110 such that the electrical conductor 110 is at least partially electrically and/or thermally insulated by the insulator 120. The wire 200, electrical conductor 110, and/or insulator 120 may include or be made from one or more degradable materials. In this manner, electronics, sensors, wiring, memory, etc. may be degradable or biodegradable. As described herein, the term "degradable" refers to being capable of decomposing such as by chemical, environmental, and/or organism action. For example, the materials may be of a composition susceptible to spontaneous breakdown over time. The materials may be degradable by the physical and/or chemical action of water or bodies of water, such as lakes, oceans, etc. Additionally or alternatively, the materials may be degradable by solar irradiation. Biodegradable materials are degradable materials.

Figure 12:
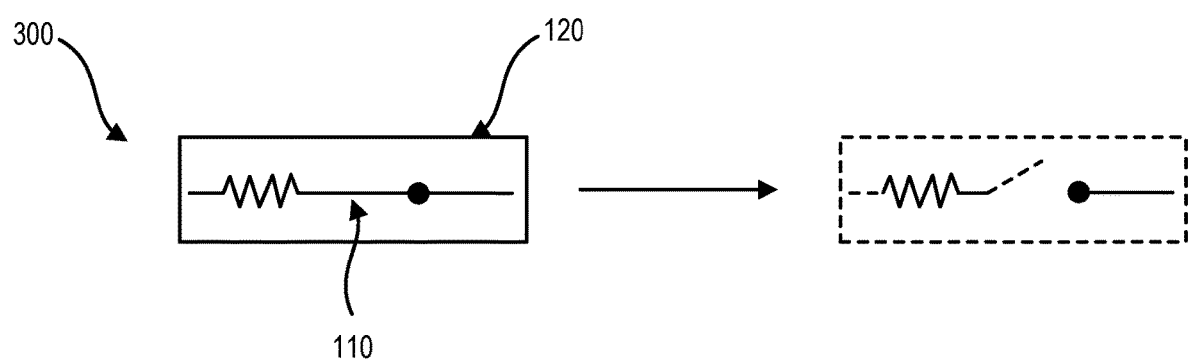
FIGS. 12-15 are schematic diagrams of example electrical devices.

FIG. 12 shows an example electrical device 300 (e.g., implantable device 100) including an electrical conductor 110 and an insulator 120. As shown in FIG. 3, the insulator 120 may be in physical contact with and/or extend at least partially about the electrical conductor 110 such that the electrical conductor 110 is at least partially electrically and/or thermally insulated by the insulator 120.

The electrical device 300, electrical conductor 110, and/or insulator 120 may include or be made from one or more degradable materials. For example, the insulator 120 may include one or more degradable materials such that degradation of the insulator 120 at least partially exposes the electrical conductor 110 to the ambient environment. In some examples, the electrical device 300 includes one or more polymers (e.g., biologically active material 130) that are degradable in an ocean environment. Alternatively, the electrical device 300 may include any material that is degradable in any environment, such as a manufacturing or automotive environment.

In some examples, the insulator 120 is responsive to one or more triggers that cause or induce degradation of the insulator 120. For example, a trigger may at least partially degrade and/or kill the biologically active material 130. Example triggers include radiation (e.g., microwave radiation, ultraviolet radiation, infrared radiation), a magnetic field, air, moisture, a temperature, and/or a temperature change (e.g., heating, cooling). In some examples, cells are heated to temperatures that cause apoptotic death (e.g. about 40° C. to about 50° C.) and/or necrotic death (e.g., about 50° C. or higher) for thermoablation.

In some examples, degradation of the insulator 120 at least partially exposes the electrical conductor 110 to at least partially diminish activity or capacity of the electrical device 300. For example, the electrical conductor 110 may be responsive to one or more triggers that cause or induce degradation of the electrical conductor 110. As shown in FIG. 3, at least a portion of the electrical conductor 110 (e.g., switch) may be configured to degrade when exposed to the ambient environment. This may confer useful designed obsolescence of the electrical device 300. Alternatively, degradation of the insulator 120 at least partially exposes the electrical conductor 110 to at least partially increase activity or capacity of the electrical device 300. For example, the electrical conductor 110 may have increased access to a target when exposed to the ambient environment.

In some examples, the insulator 120 is responsive to a first trigger, and the electrical conductor 110 is responsive to a second trigger that is different from the first trigger. Alternatively, the insulator 120 and electrical conductor 110 may be responsive to the same trigger.

Figure 13:
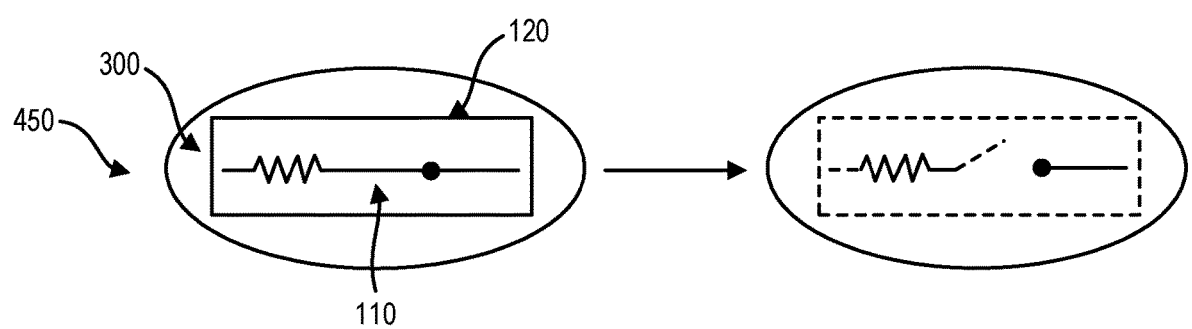

FIG. 13 shows the electrical device 300 implanted in an organism 450. The electrical device 300 may be implanted or inserted, for example, in a human (e.g., for medical care) or animal (e.g., for veterinary care). The electrical device 300 may be implanted using a robotic system, which may include any of the robotic systems described above herein, for example. In some examples, the electrical device 300, electrical conductor 110, and/or insulator 120 includes one or more materials configured to degrade and/or resorb in the organism 450. For example, the insulator 120 may include one or more biodegradable materials such that degradation of the insulator 120 at least partially exposes the electrical conductor 110 to the organism 450.

In some examples, the electrical device 300 is configured such that a conductance of the electrical conductor 110 decreases in vivo. For example, degradation of the insulator 120 at least partially exposes the electrical conductor 110 to at least partially diminish activity or capacity of the electrical device 300. As shown in FIG. 4, at least a portion of the electrical conductor 110 (e.g., switch) may be configured to degrade when exposed to the organism 450. This may confer useful designed obsolescence of the electrical device 300. Alternatively, the electrical device 300 may be configured such that the conductance of the electrical conductor 110 increases in vivo. For example, degradation of the insulator 120 at least partially exposes the electrical conductor 110 to at least partially increase access to the organism 450. In some examples, the electrical device 300 include myelin or a myelin-like material (e.g., biologically active material 130).

Figure 5:
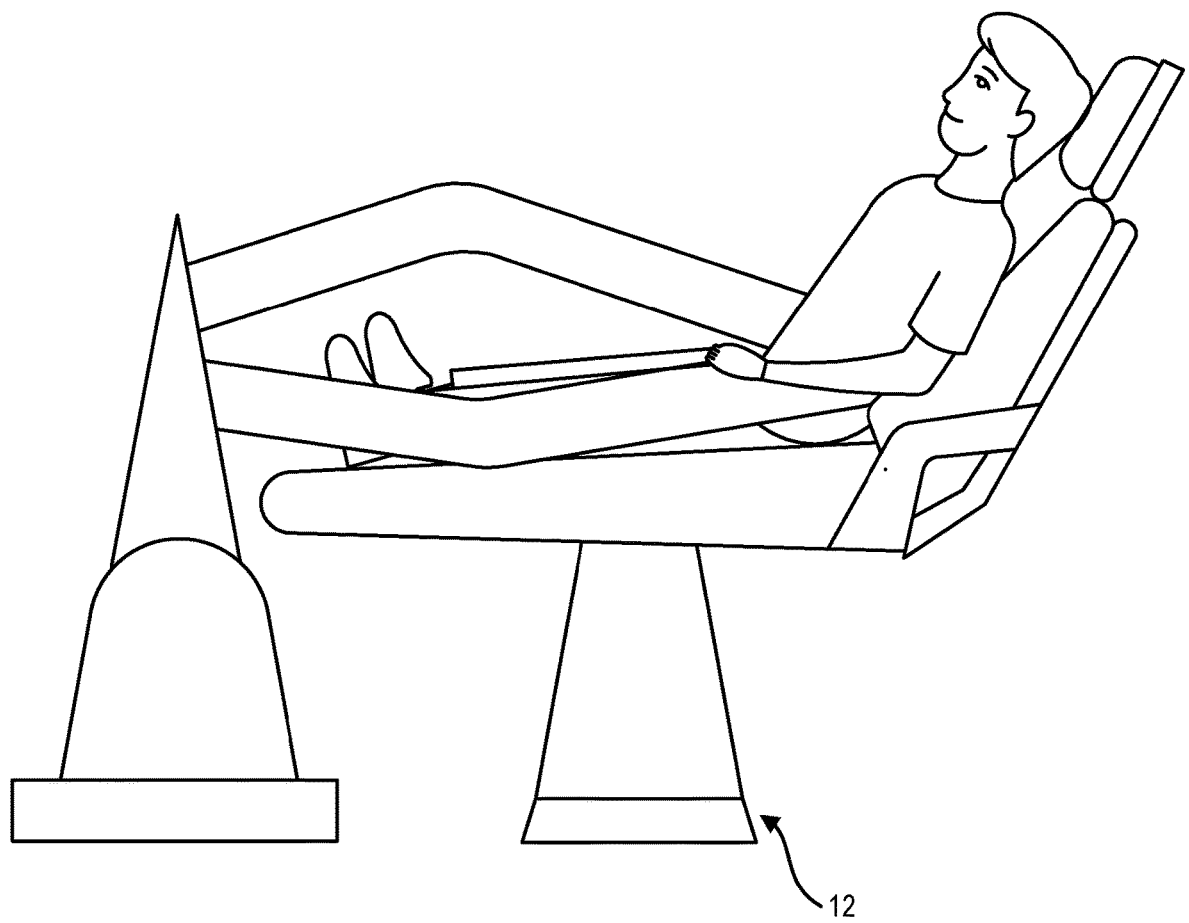
FIG. 5 is an illustration of a patient on an operating table of the present disclosure.
Figure 14:
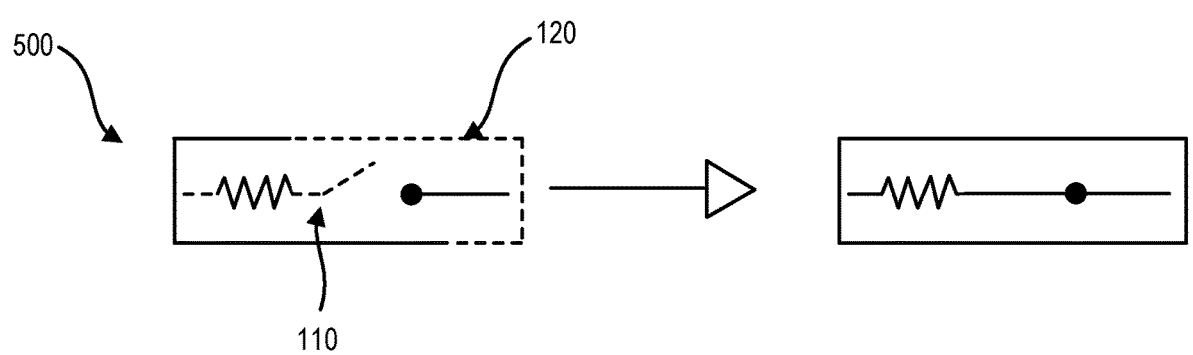

FIG. 14 shows an example electrical device 500 (e.g., implantable device 100, electrical device 300) including an electrical conductor 110 and an insulator 120. As shown in FIG. 5, the insulator 120 may be in physical contact with and/or extend at least partially about the electrical conductor 110 such that the electrical conductor 110 is at least partially electrically and/or thermally insulated by the insulator 120.

Figure 15:
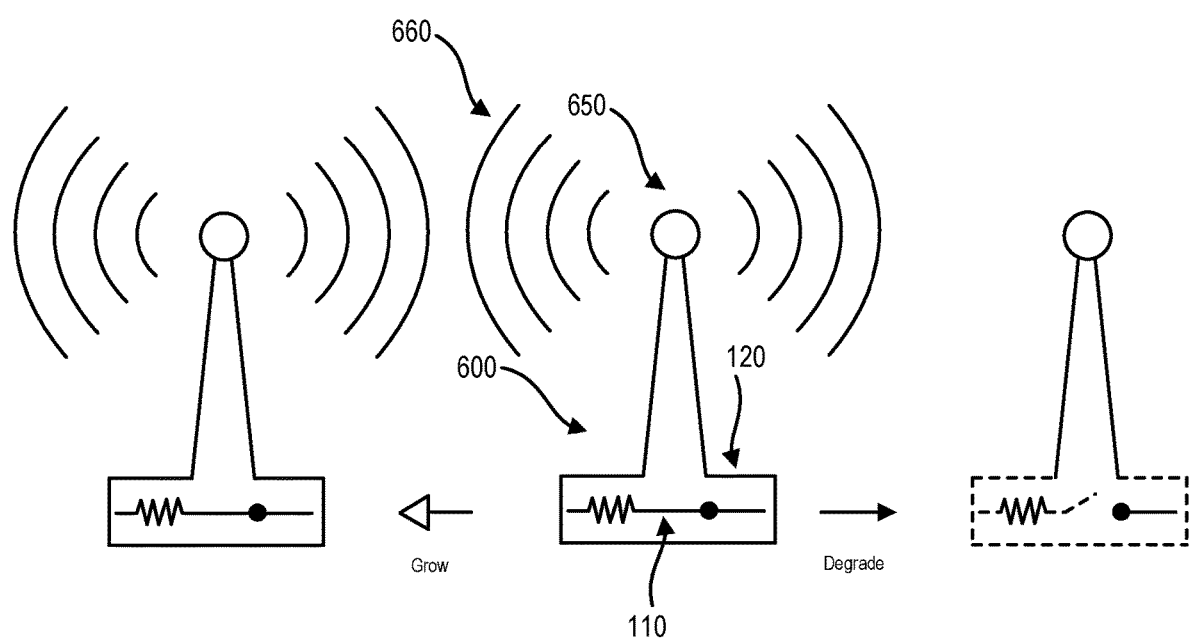

The electrical conductor 110 and/or insulator 120 may include or be made from one or more regenerative materials. The electrical conductor 110 and/or insulator 120 may include or contain, for example, one or more live cells that grow, reproduce, and/or differentiate such that the electrical conductor 110 and/or insulator 120 grow and/or repair themselves. The electrical conductor 110 and/or insulator 120 may be configured to repair themselves from an at least partially inactive state. As shown in FIG. 15, at least a portion of the electrical conductor 110 (e.g., switch) may be restored and/or increase capacity of the electrical device 500.

In some examples, the electrical conductor 110 and/or insulator 120 are responsive to one or more triggers that cause or induce growth, reproduction, and/or differentiation of the electrical conductor 110 and/or insulator 120. For example, a trigger may at least partially stimulate, restore, and/or revive the biologically active material 130. Example triggers include radiation (e.g., microwave radiation, ultraviolet radiation, infrared radiation), a magnetic field, a temperature, and/or a temperature change (e.g., heating, cooling). In some examples, the insulator 120 is responsive to a first trigger, and the electrical conductor 110 is responsive to a second trigger that is different from the first trigger. Alternatively, the insulator 120 and electrical conductor 110 may be responsive to the same trigger.

FIG. 15 shows an example electrical device 600 (e.g., implantable device 100, electrical device 300, electrical device 500) including an electrical conductor 110 and an insulator 120. As shown in FIG. 6, the insulator 120 may be in physical contact with and/or extend at least partially about the electrical conductor 110 such that the electrical conductor 110 is at least partially electrically and/or thermally insulated by the insulator 120. The electrical device 600 may include or may be in operational connection with a communication device 650 (e.g., transmitter, receiver, transceiver). In some examples, the communication device 650 is used for wireless communication. In some examples, the insulator 120 provides biological electromagnetic shielding. In some examples, the communication device 650 creates or receives one or more signals 660.

The electrical conductor 110 and/or insulator 120 may include or be made from one or more degradable materials. In some examples, degradation of the insulator 120 may at least partially diminish activity or capacity of the electrical device 600 and/or communication device 650 to decrease a strength of the signal 660. For example, degradation of the insulator 120 may at least partially expose the electrical conductor 110, which may cause at least partial degradation of the electrical conductor 110. Alternatively, degradation of the insulator 120 may at least partially increase activity or capacity of the electrical device 600 and/or communication device 650 to increase a strength of the signal 660. For example, degradation of the insulator 120 may at least partially expose the electrical conductor 110, which may provide increased functionality of the electrical conductor 110.

In some examples, the electrical conductor 110 and/or insulator 120 includes or is made from one or more generative materials. The electrical conductor 110 and/or insulator 120 may include or contain, for example, one or more live cells configured to reproduce and/or cause at least partial growth of the electrical conductor 110 and/or insulator 120. In this manner, the electrical device 600, electrical conductor 110 and/or insulator 120 may be configured to repair and/or grow themselves. In some examples, repair and/or growth of the electrical conductor 110 and/or insulator 120 at least partially restore and/or increase activity or capacity of the electrical device 600 and/or communication device 650 to increase a strength of the signal 660. Alternatively, repair and/or growth of the electrical conductor 110 and/or insulator 120 may at least partially diminish activity or capacity of the electrical device 600 and/or communication device 650 to decrease a strength of the signal 660.

In this manner, a strength of signals 660 may be selectively increased or decreased. Additionally, electricity may be selectively routed (e.g., control circuit). Additionally, corrosion may be selectively discouraged or encouraged. In this manner, materials (e.g., metals, polymers) may be selectively protected, released into the environment, and/or allowed to decay.

Figure 16:
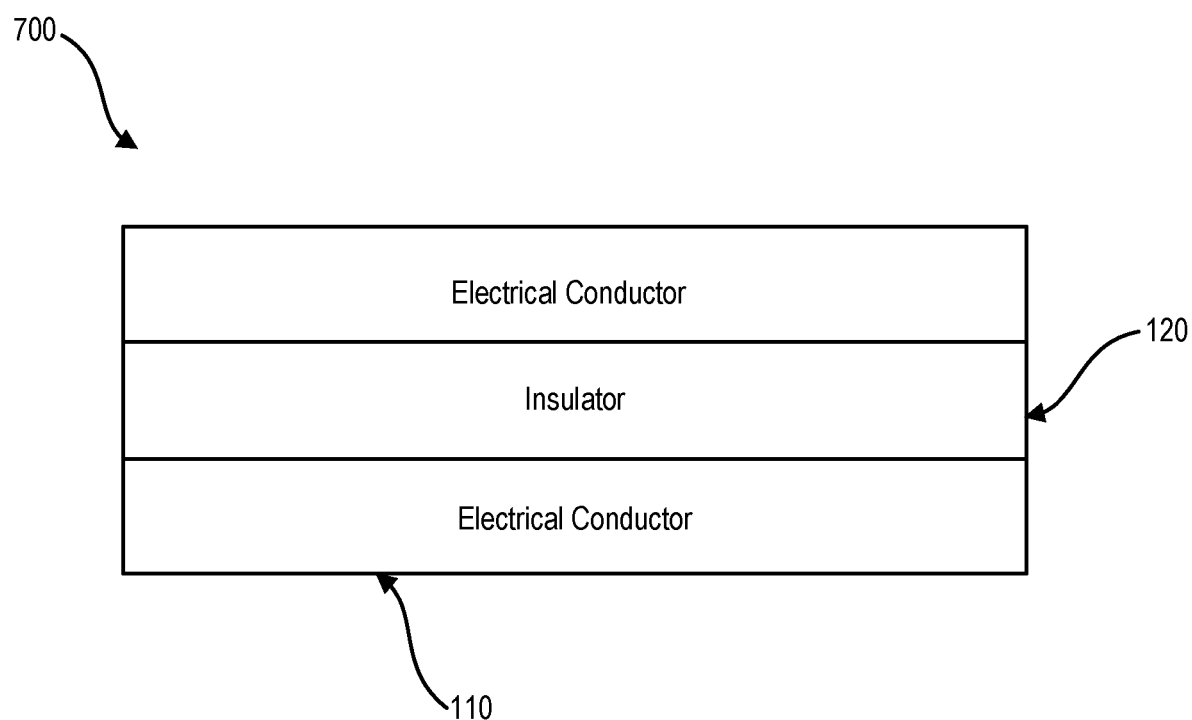
FIG. 16 is a block diagram of an example capacitor.

FIG. 16 shows an example capacitor 700 that may be used with or included in the implantable device 100, electrical device 300, and/or electrical device 500. The capacitor 700 is configured to store an electric charge. In this manner, the capacitor 700 may be used as a rechargeable power source.

As shown in FIG. 16, the capacitor 700 includes a pair of electrical conductors 110 and an insulator 120 disposed therebetween. The insulator 120 may function, for example, as a dielectric for the capacitor 700. Additionally, the capacitor 700 may be coupled to another electrical conductor 110. In some examples the electrical conductor 110 is or includes a conductive film. The conductive film may include a solution of one or more electrolytes (e.g., sodium) and/or a suspension of one or more of copper, silver, gold, platinum, carbon nanotubes, and graphene.

The implantable device 100, electrical conductor 110, insulator 120, biologically active material 130, electrical device 300, electrical device 500, electrical device 600, and/or capacitor 700 may be manufactured using any means known to those skilled in the art. For example, the implantable device 100, electrical conductor 110, insulator 120, biologically active material 130, electrical device 300, electrical device 500, electrical device 600, and/or capacitor 700 may be produced or deposited using a three-dimensional ("3D") printer.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

Microplastic Filter

The subject matter described herein relates to filters and, more particularly, to microplastic filtration systems. Micro particles and pollution into a water system, which is then ingested by animals and people or into nutrients can damage, destroy, or create blockages as the micro particles are linked together. The micro particles can go through celluloid systems, digestive systems, and filters very easily. The micro particles can damage or destroy biologic living structures, but they can also over time occlude filters and lead to backup, therefore, infections, waste, smell, debris, etc. Micro particles can be used for heating also for industry and multiple clothing systems. For example, Micro particles, such as microfibers, are used in a number of clothes that people wear and use, which are released into the water system or irrigation system each year. When combine with additional macro particles, they can occlude and then lead to tremendous issues with debris, clogging, bacteria, and severe smell as well as the ability to damage or clog the system structures. Further, micro plastics have become one of the most prevalent types of marine debris found, and one of major contributor is from washing and drying of clothes with synthetic fibers. These plastics are extremely small (<5 mm to 10 nM) and difficult to filter. However, the plastics are much larger than the surrounding water molecule which are around 0.275 nM.

In accordance with the present disclosure, example microplastic filtration systems may include a body through which a fluid or liquid may be channeled, and one or more transducers coupled to the body. The transducers may be used to generate pressure waves for removing particulates from the fluid or liquid. For example, the pressure waves may urge or displace microplastic toward or away from one or more channels within the body. In this manner, examples described herein facilitate decreasing or eliminating fouling issues encountered with traditional filters. The examples described herein may be used in one or more systems, such as heating, ventilation, and air conditioning (HVAC) systems; washing machines, and/or effluent systems.

Figure 17:
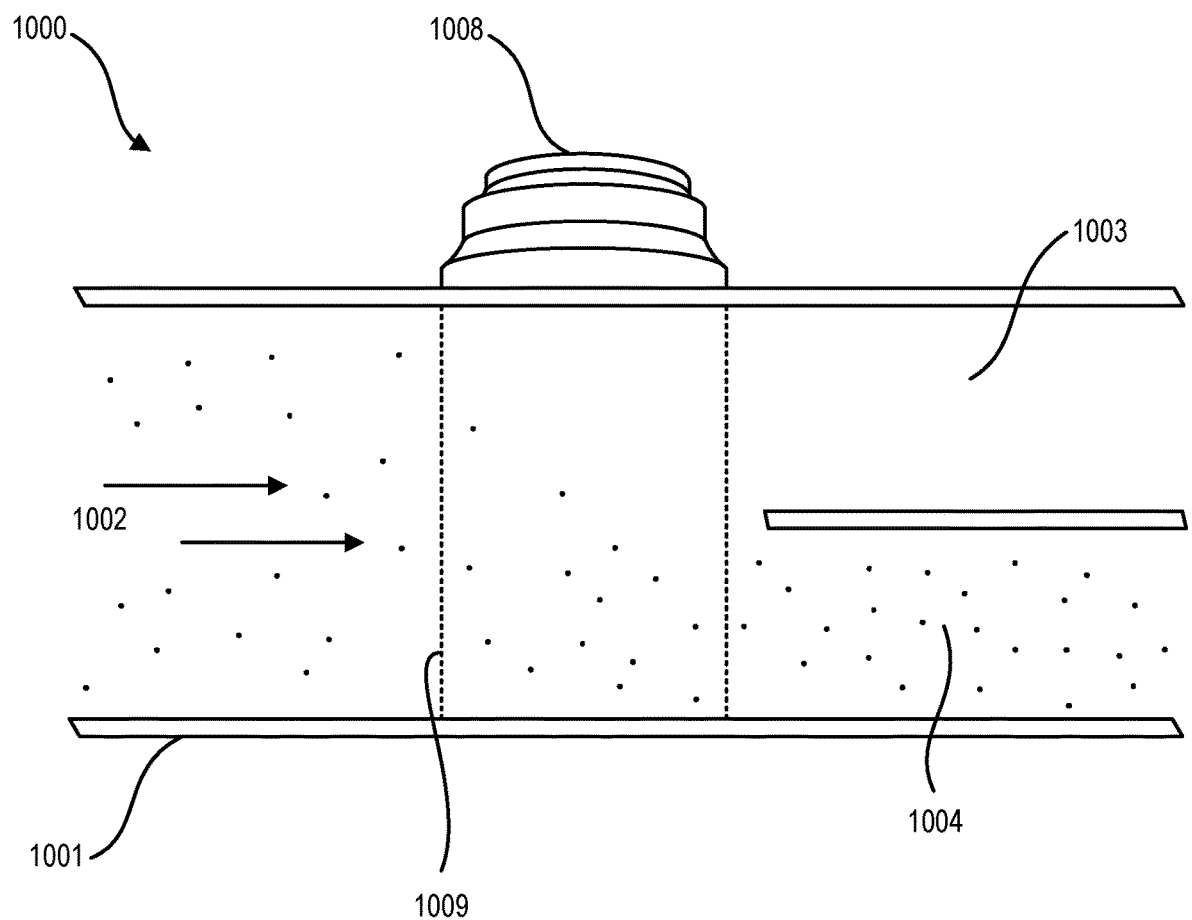
FIG. 17 shows a schematic view of an example microplastic filtration system.

FIG. 17 shows an example microplastic filtration system 1000 including a body 1001. The body 1001 has a plurality of inner walls or surfaces that define one or more channels through which a fluid or liquid may be channeled. A liquid flow 1002, for example, may be channeled through at least a first channel 1003 and a second channel 1004 defined in the body 1001. The inner surfaces of the body 1001 may be positioned and/or oriented in any direction that enables the microplastic filtration system 1000 to function as described herein. In some examples, a filter is positioned at, adjacent to, and/or downstream from the second channel 1004 to collect particulates in the liquid flow 1002. Example filters include, without limitation, charcoal filters, reverse osmosis, electrostatic, water ionizers, and other filters known in the art.

At least one transducer 1008 is coupled to the body 1001. As shown in FIG. 17, a transducer 1008 may be coupled to an outer wall or surface of the body 1001. Alternatively, the transducer 1008 may be coupled to any portion of the body 1001 and/or oriented in any direction that allows the microplastic filtration system 1000 to function as described herein.

The transducer 1008 is configured to generate or create a pressure wave 1009 in the liquid flow 1002. The pressure wave 1009 may move, for example, transversely across the liquid flow 1002. In some examples, the transducer 1008 creates a pressure wave 1009, specifically a standing pressure wave, having a frequency that ensures that there are no nodes, points of little or no amplitude, in the liquid flow 1002. Alternatively, the transducer 1008 may be configured to create a pressure wave 1009 having any frequency that enables the microplastic filtration system 1000 to function as described herein. While the preferred embodiment uses ultrasonic transducers, other embodiments can use audible or subsonic frequencies.

The transducer 1008 is powered at a level such that the pressure wave 106 displaces at least some particulates in the liquid flow 1002. The particulates may be urged or moved, for example, away from the first channel 1003 and/or towards or into the second channel 1004. In this manner, a portion of the liquid flow 1002 channeled through the first channel 1003 has a lower percentage of particulates than that of a portion of the liquid flow 1002 channeled through the second channel 1004. Alternatively, the particulates may be urged or moved towards or into the first channel 1003 and/or away from the second channel 1004.

Figure 18:
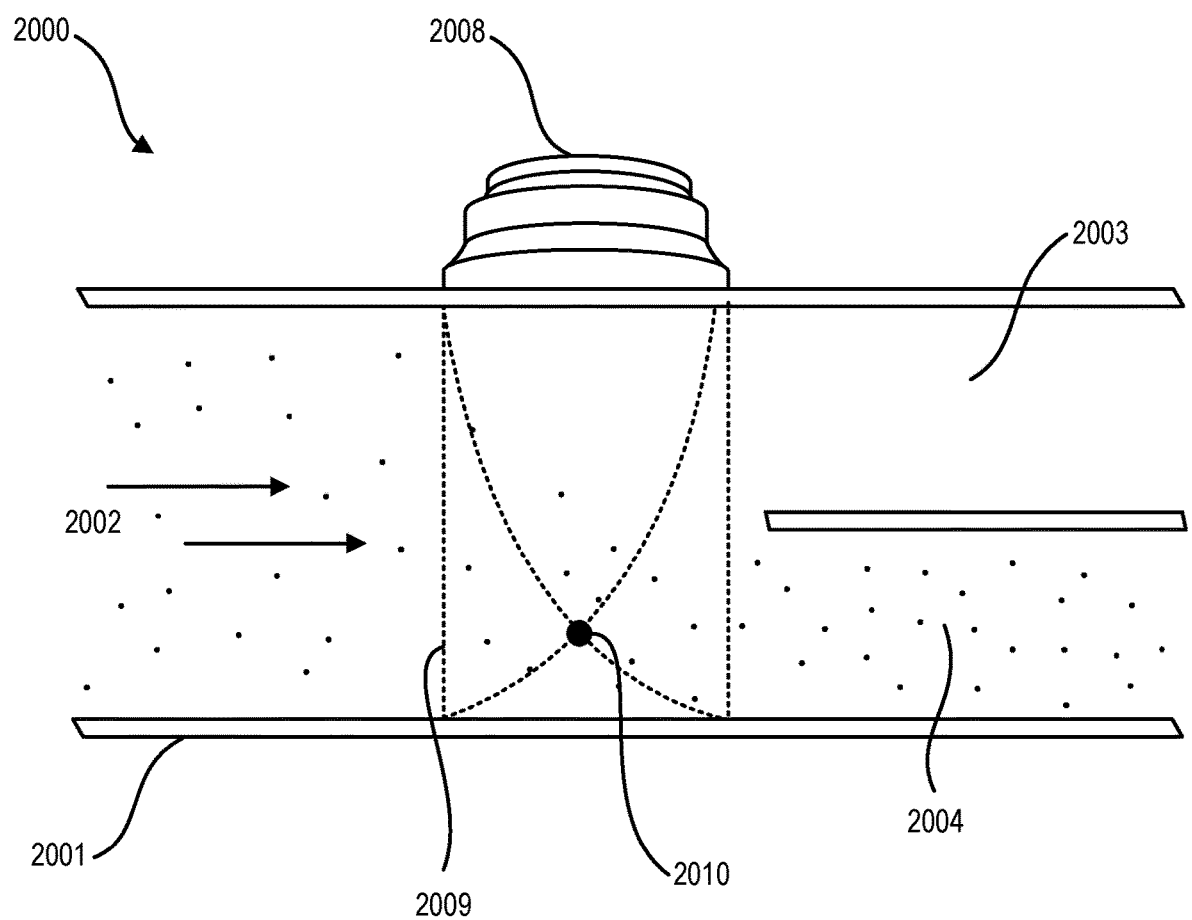
FIG. 18 shows a schematic view of another example microplastic filtration system.

FIG. 18 shows another example microplastic filtration system 2000 including a body 2001. Like the body 1001, the body 2001 has a plurality of inner walls or surfaces that define one or more channels through which a fluid or liquid may be channeled. A liquid flow 2002, for example, may be channeled through at least a first channel 2003 and a second channel 2004 defined in the body 2001. The inner surfaces of the body 2001 has may be positioned and/or oriented in any direction that enables the microplastic filtration system 2000 to function as described herein.

At least one transducer 2008 is coupled to the body 2001. As shown in FIG. 18, a transducer 2008 may be coupled to an outer wall or surface of the body 2001. Alternatively, the transducer 2008 may be coupled to any portion of the body 2001 and/or oriented in any direction that allows the microplastic filtration system 2000 to function as described herein.

The transducer 2008 is configured to generate or create a pressure wave 2009 in the liquid flow 2002. The pressure wave 2009 may move, for example, transversely across the liquid flow 2002. In some examples, the pressure wave 2009 is a standing wave with a single node 2010, where there is a reduced displacement or pressure variation. Particulates in the liquid flow 2002 generally tend or are biased to move toward lower pressure areas within the liquid flow 2002 (e.g., node 2010).

The transducer 2008 is powered at a level such that the pressure wave 2009 displaces at least some particulates in the liquid flow 2002. In some examples, the node 2010 is aligned with the second channel 2004 such that at least a portion of the particulates displaced by the pressure wave 2009 is directed towards or into the second channel 2004. In this manner, a portion of the liquid flow 2002 channeled through the first channel 2003 has a lower percentage of particulates than that of a portion of the liquid flow 2002 channeled through the second channel 2004. Alternatively, the node 2010 may be aligned with the first channel 2003.

Figure 19:
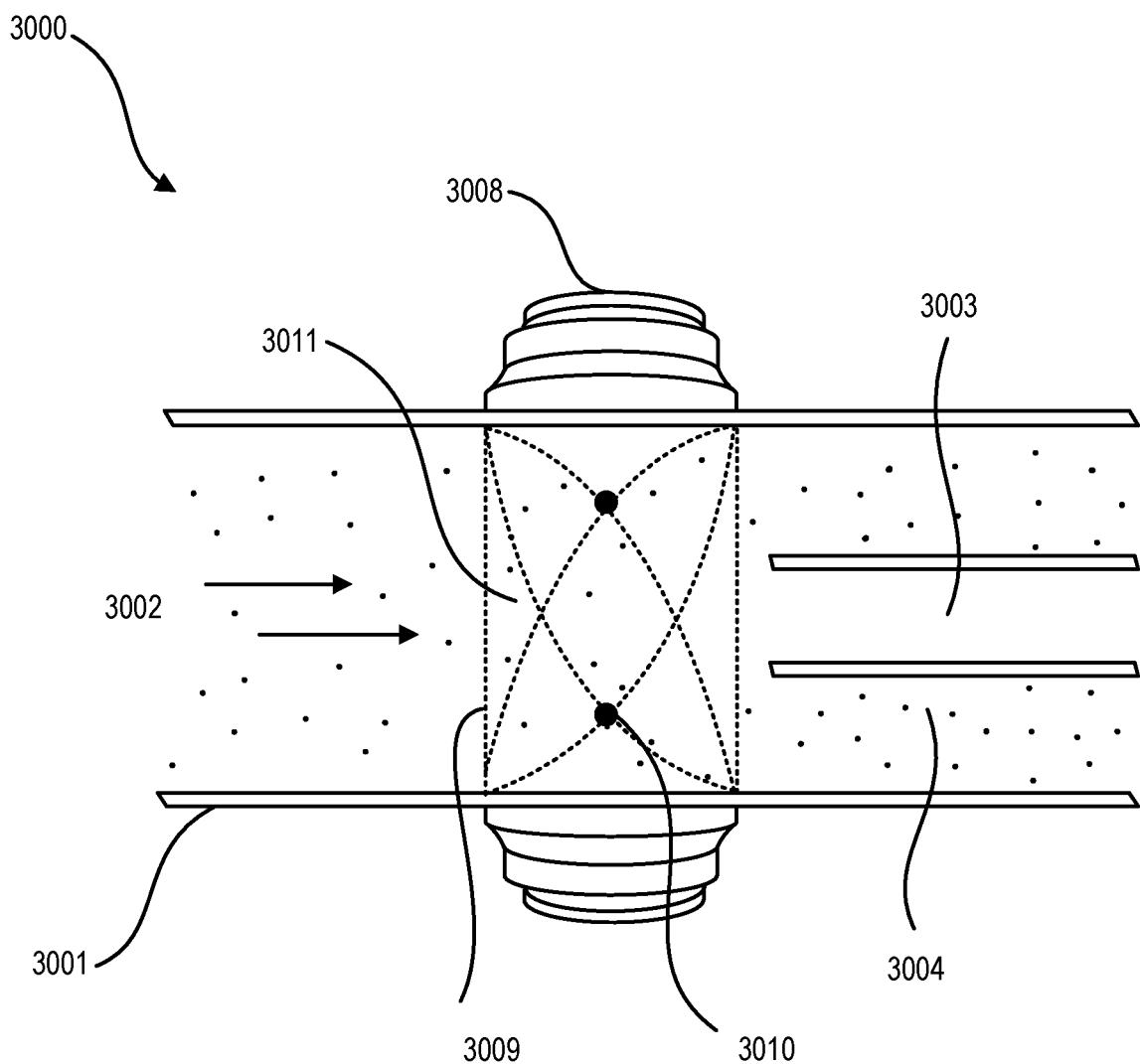
FIG. 19 shows a schematic view of yet another example microplastic filtration system.
Figure 20:
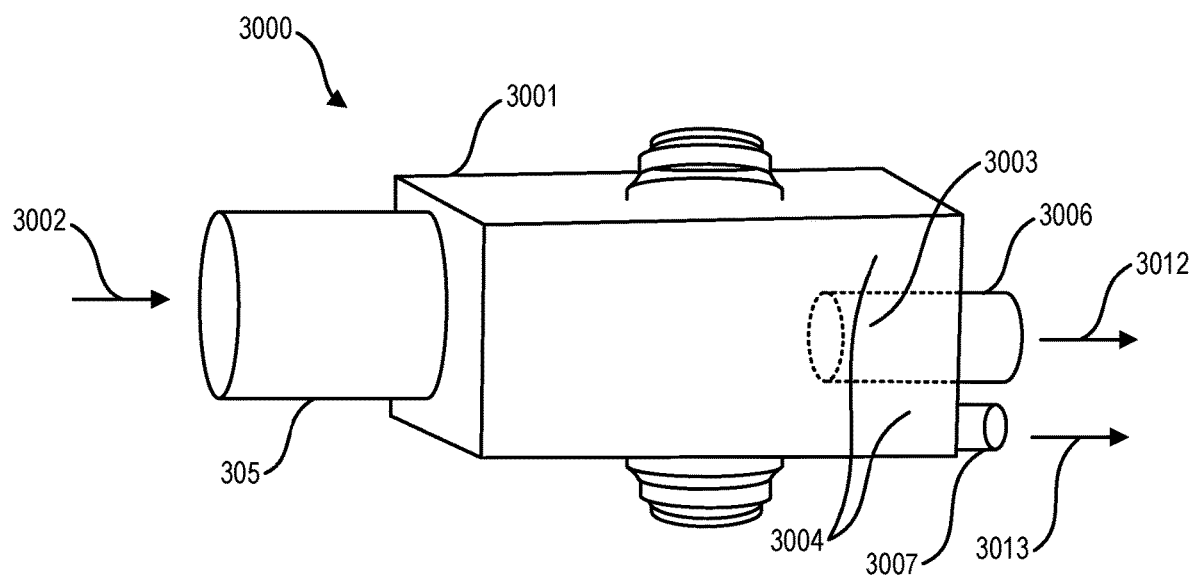
FIG. 20 shows a perspective view of the microplastic filtration system shown in FIG. 19.
Figure 21:
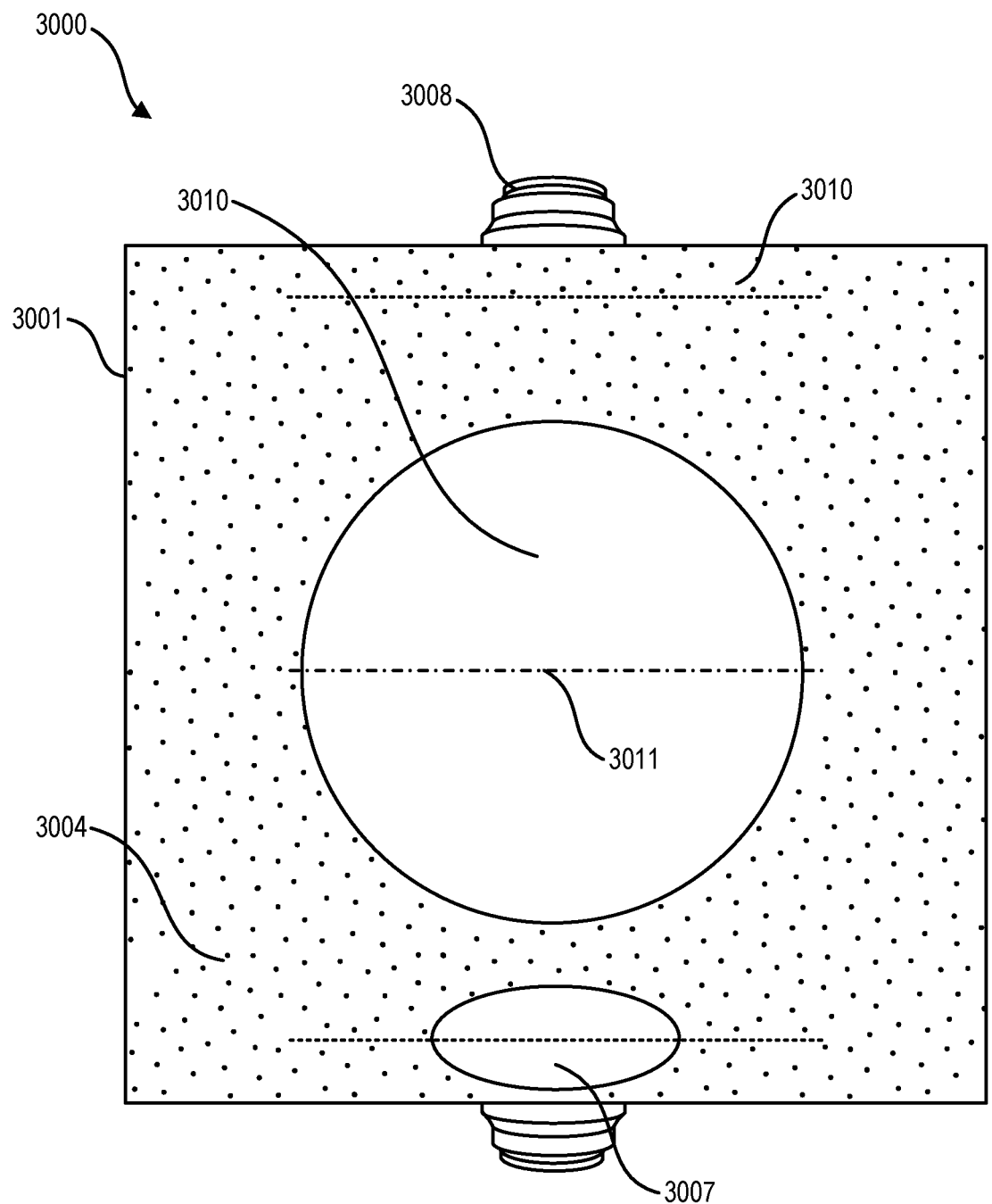
FIG. 21 shows a transverse cross-section view of the microplastic filtration system of FIG. 19.

FIGS. 19-21 show yet another example microplastic filtration system 3000 including a body 3001. Like the body 1001 and/or body 2001, the body 3001 has a plurality of inner walls or surfaces that define one or more channels through which a fluid or liquid may be channeled. A liquid flow 3002, for example, may be channeled through at least one or more first channels 3003 and one or more second channels 3004 defined in the body 3001. In some examples, the liquid flow 3002 enters the body 3001 through an inlet 3005 (shown in FIG. 19) and exits the body 3001 through a first outlet 3006 (shown in FIG. 20) in fluid communication with the first channel 3003 or a second outlet 3007 (shown in FIG. 21) in fluid communication with the second channel 3004. The second outlet 3007 may direct the fluid to a filter, a heating chamber (e.g., for melting or agglomerating microplastics), and/or a collection tank including bacteria (e.g., for breaking down the particulates). In some examples, the second outlet 3007 includes or uses an ultraviolet or other identification system to activate a valve system for selectively directing the fluid to the filter, heating chamber, and/or collection tank. Additionally, or alternatively, a check valve system at the first outlet 3006 and/or second outlet 3007 may be used to facilitate reducing contamination from backflow. The inner surfaces of the body 3001 has may be positioned and/or oriented in any direction that enables the microplastic filtration system 3000 to function as described herein.

A plurality of transducers 3008 are coupled to the body 3001. As shown in FIGS. 19-21, a pair of transducers 3008 may be coupled to an outer wall or surface on opposite sides of the body 3001. In some examples, the transducers 3008 are generally aligned with each other. Alternatively, the transducers 3008 may be coupled to any portion of the body 3001 and/or oriented in any direction that allows the microplastic filtration system 3000 to function as described herein. In some examples, the inlet 3005 includes or uses an ultraviolet or other identification system to activate the transducers 3008 upon identifying one or more particulates.

The transducers 3008 are configured to generate or create one or more pressure waves 3009 in the liquid flow 3002. The pressure waves 3009 may move, for example, transversely across the liquid flow 3002. In some examples, the pressure wave 3009 is a standing wave with one or more nodes 3010, where there is a reduced displacement or pressure variation, and one or more antinodes 3011, where there is an increased displacement or pressure variation. Particulates in the liquid flow 3002 generally tend or are biased to move toward lower pressure areas within the liquid flow 3002 (e.g., node 3010) and/or away from higher pressure areas within the liquid flow 3002 (e.g., antinode 3011).

The transducer 3008 is powered at a level such that the pressure wave 3009 displaces at least some particulates in the liquid flow 3002. In some examples, the nodes 3010 are aligned with the second channels 3004 such that at least a portion of the particulates displaced by the pressure wave 3009 is directed towards or into the second channels 3004. Additionally or alternatively, the antinodes 3011 may be aligned with the first channel 3003 such that at least a portion of the particulates displaced by the pressure wave 3009 is directed away from the first channel 3003. In this manner, a portion of the liquid flow 3002 channeled through the first channel 3003 has a lower percentage of particulates than that of each portion of the liquid flow 3002 channeled through a second channel 3004, such that a filtered output 3012 is discharged or released from the first outlet 3006 and a waste output 313 is discharged or released from the second outlet 3007. Alternatively, a node 3010 may be aligned with a first channel 3003 and/or an antinodes 3011 may be aligned with a second channel 3004.

Figure 22:
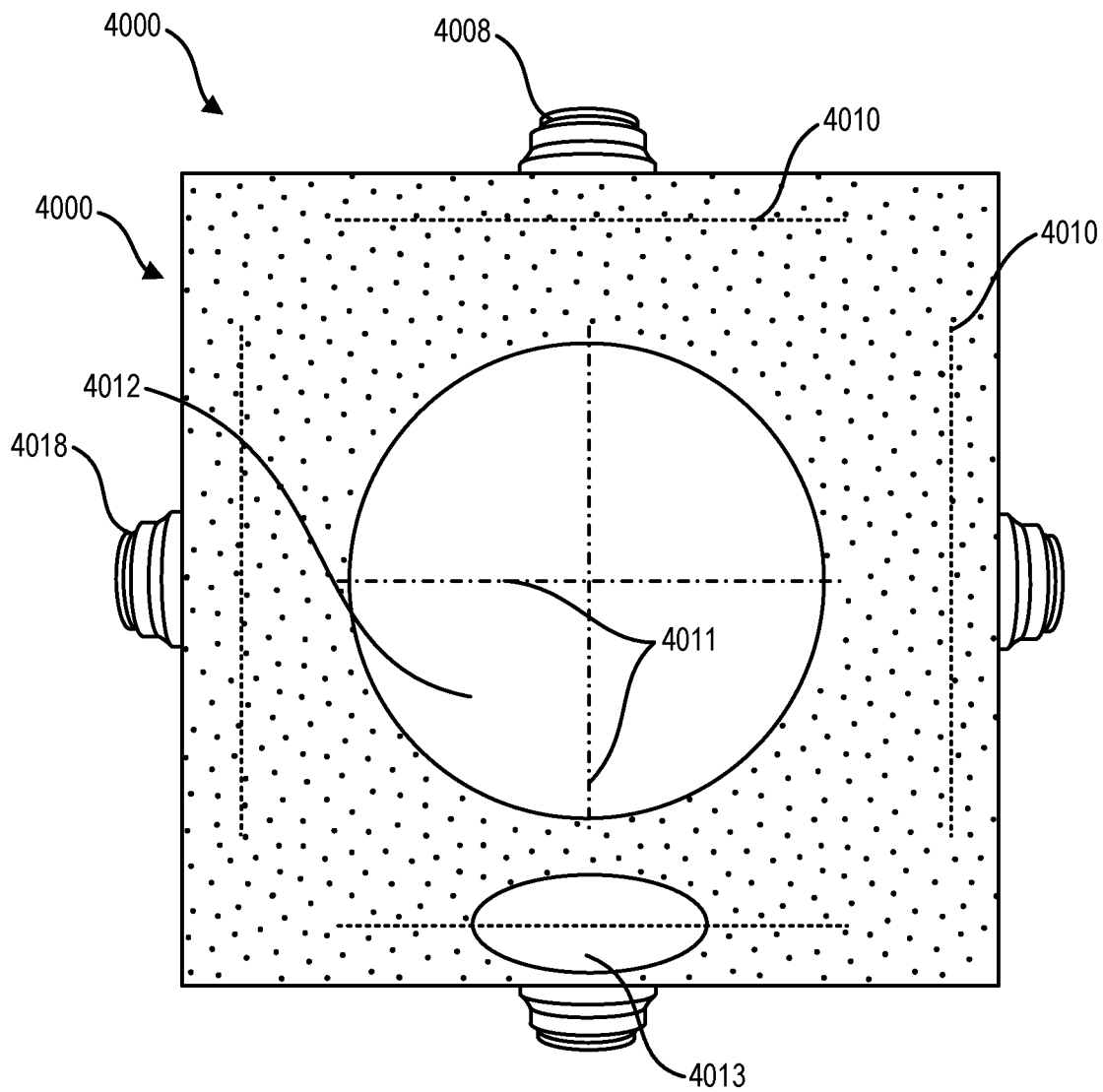
FIG. 22 shows a transverse cross-section view of yet another example microplastic filtration system.

FIG. 22 shows yet another example microplastic filtration system 4000 including a body 4001. Like the body 1001, body 2001, and/or body 3001, the body 4001 has a plurality of inner walls or surfaces that define one or more channels through which a fluid or liquid may be channeled. In some examples, a liquid flow exits the body 4001 through a first outlet 4012 or a second outlet 4013. The inner surfaces of the body 4001 has may be positioned and/or oriented in any direction that enables the microplastic filtration system 4000 to function as described herein.

A plurality of transducers 4008, 4018 are coupled to the body 4001. As shown in FIG. 22, a first pair of transducers 4008 may be coupled to an outer wall or surface on first opposite sides of the body 4001, and a second pair of transducers 4018 may be coupled to an outer wall or surface on second opposite sides of the body 4001 generally orthogonal or perpendicular to the first opposite sides. In some examples, the transducers 4008, 4018 are generally aligned with each other. Alternatively, the transducers 4008, 4018 may be coupled to any portion of the body 4001 and/or oriented in any direction that allows the microplastic filtration system 4000 to function as described herein.

The transducers 4008, 4018 are configured to generate or create one or more pressure waves in the liquid flow. In some examples, the pressure waves are standing waves with a plurality of nodes 4010, where there is a reduced displacement or pressure variation, and a plurality of antinodes 411, where there is an increased displacement or pressure variation.

The transducers 4008, 4018 are powered at one or more levels such that the pressure waves displace at least some particulates in the liquid flow. In some examples, a filtered output is discharged or released from the first outlet 4012 and a waste output is discharged or released from the second outlet 4013. Alternatively, a waste output may be discharged or released from the first outlet 4012 and/or a filtered output may be discharged or released from the second outlet 4013.

Examples described herein may be used to filter any combination of particulates from a fluid or liquid (e.g., water). Fluid or liquid being filtered using examples described herein may be effluent from manufacturing, cleaning, and industrial processes. Particulates may include inorganic and/or organic debris, such as plastics, microplastics, microfibers, parasites, bacteria, and the like. The size of particulates may be less than about 10 micrometers (μmm), less than about 5 μm, less than about 1 μm, less than about 500 nanometers (nm), less than about 1000 nm, less than about 10 nm, or less than about 1 nm. The percentage of the displaced particulates may be greater than about 50%, greater than about 60%, greater than about 70%, greater than about 80%, greater than about 90%, greater than about 95%, greater than about 99%, or greater than about 99.9% of the particulates in the fluid or liquid flow. Filtered water could also be held for further processing to remove microplastics. This could include a centrifuge, static charging of particles such that they are attracted to other particles or a section of the filter, a heating element to bond the plastic particles, distilling, or evaporating the water off.

For retrievable of micro particles, a gelatin could be used to attach to the micro particles. The gelatin could be an agglutinin agent that would allow the micro particles to adhere together much like jello, such that microfibers are hidden in this jello. Micro particles would become stuck and adhere. The gelatin and micro particles could be mechanically removed after creating a larger structure that is more easily structured or removed. The gelatin and micro particles could be removed manually or robotically, which could be cleared on regular intervals. Regular intervals could be controlled via a timing system or be controlled when the gelatin itself becomes too thick or too coated with particles. It could filter through a centrifuge, but it could allow the particles to agglutinate and then catch the material through effluent water either through a centrifuge and/or filter and/or electric charges or magnetic charges. These are catching into a gelatin that would allow one to remove this material and capture it. This could be done through remote control or automatic. It could be Bluetooth wireless or robotically utilized to sweep and remove gel or excessive particles once they are agglutinated or become thick enough.

Transducers described herein may convert electrical energy to acoustic energy (e.g., mechanical vibrations). Examples described herein may include any arrangement of transducers, which may operate independently or cooperatively, to generate one or more pressure waves. The transducers may be situated, for example, along an axial length of the body and/or circumferentially around a perimeter of the body. Example transducers include a piezo element, a Langevin stack, or other known elements in the art.

In an alternative embodiment (not shown), a robotic system with mop-head like qualities could be used to sweep and charge the particulates in the fluid or liquid instead of the transducers. As the robotic system sweeps through either a centrifuge or the fluid, multiple filaments through magnetics or radiofrequency or electrical charges would catch microfibers through centrifuge and possibly create a gel once the microfibers are agglutinated. Again, multiple fibers and multiple transducers could be floating through the fluid or spinning through the fluid to catch these particulates.

Various portions of the bodies described herein may be fabricated from one or more materials to facilitate controlling the pressure waves. For example, the bodies may be configured to absorb and/or reflect pressure waves propagating through the fluid or liquid. Examples described herein may be an add-on feature to existing systems. Alternatively, the examples may be built-in or integrated into a larger system.

Microplastic filtration systems, as described in the present disclosure, can be placed on washing machines of industrial or family to capture microfibers. Alternatively, the microplastic filtration systems could also be used in water treatment centers/systems or even in general water to filter on a repetitive basis, capturing micro plastics by combining either filters electrical or magnetic management, so they can make these smaller particles either destroyed or create them into larger particles which can then be removed and then treated as macro particles.

Particles can also be enhanced with certain types of chemicals. The particles would adhere them together and then they could be captured in a filter and potentially destroyed through thermal, electrical, or other water treatment systems. The microplastic filter can be used thermally, electrically, or magnetically, as previously described.

Particles as they are being washed or treated could have chemical drugs or charges added to them either as the clothing is made or after as they are getting washed so these particular debris are captured. As the particles bond together, they create smaller particles bonding with larger fibers. The particles would be trapped either with magnetic, electrical, or other chemicals. Once trapped, the particles are then caught onto a larger filter. These filters either can be removed one by one or the filter can be repetitively scrapped with mechanical scrapping. One could use robotic systems to remove these filters and then treat them as macro particles.

The microfiber could also be casting away. The microfibers would be agglutinated together so as one is washing or agglutinating and they are captured possibly through multi fiber layer. If the filters are too fine, however, there would be significant water backlog and back pressure; therefore, these filters need special treatment programs and prevention of damage, so particles will not go into general water systems. This could be treated with any washer/dryer systems. The particles could be captured through air, water combination and with use of specific kinds of thermal filters or agglutination with chemical and/or thermal to treat this so they would "stick" to filters or surfaces so they can be easily removed as larger particles and then treated either by burning or ecologically safe methods to remove micro plastics from the environment. This could also be treated with a combination of filters or electromagnetic chemical. They would agglutinate together creating larger particles and these would be removed. Once there is a secondary wash system so one to water from the washing system for example leads into a second container system where the water sits and this water sitting could be secondarily treated with agglutinate agent or chemical causing these particles to bond together in a filter. These would then be removed as larger particle, treated, or burned. They would be bond together, treated, and removed through this. Secondary filter could be placed on one's washer/dryer system or any home septic system. After it is treated through water/air, these are treated and permanently removed with a secondary tank or secondary system as it filters out of the washer systems.

In accordance with this disclosure, separation of micro plastic particles should be on a scale that would be required for residential or commercial treatment of effluent, which will require a large energy density and a large treatable cross section. To create a larger treatment area, or more collimated beams will be used to create treatment that will be described further described in individual examples.

All of the examples work on by using pressure wave created by the transducers to manipulate suspended particles in the effluent. Density of the particles determines an amount that the particles are affected by the standing wave. Higher density particles, which are effected more by the acoustic pressures, will gather in the nodes while lower density particles will tend not to be effected.

Figure 25:
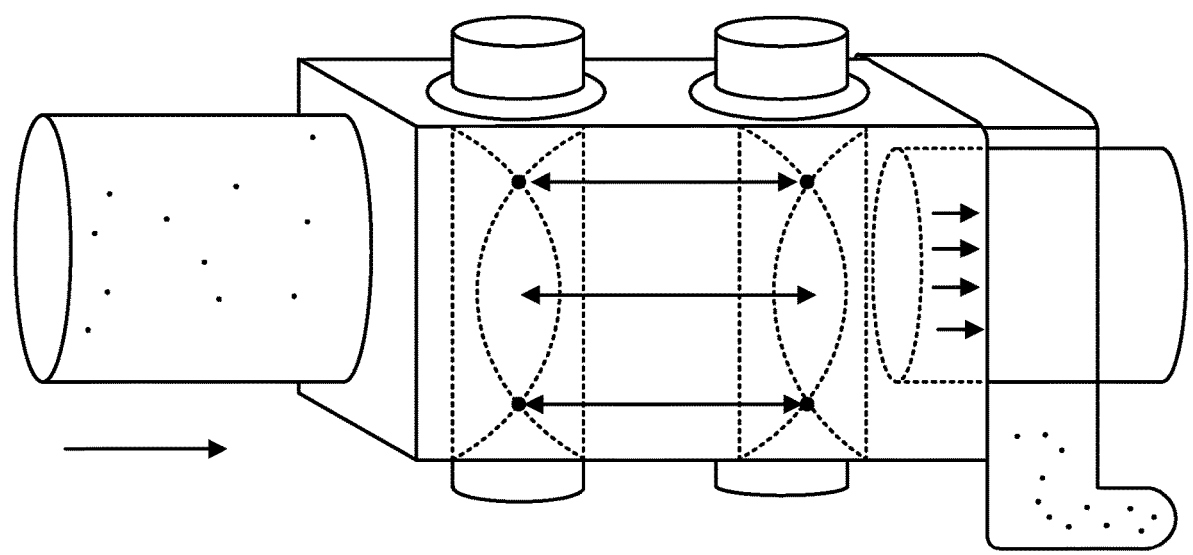
FIG. 25 is an illustration of a microplastic filtration system including two transducers on perpendicular sides.

One embodiment of the filter would have an input on one side from a clothes washer or other water source. As the water flows through the filter for separation, there will be one or more sets of matching transducers that will be used to create one or more standing waves with the nodes near the outer edges of the filter. As best shown in FIG. 25, another embodiment could have a second set of transducers on perpendicular sides so that there is a node out each outer wall of the filter. It is also considered that more than 4 transducers could be used to create a single standing wave pattern. The energy level required and the amount of standing waves required in these filters would be determined by the flow rate of the effluent through the filter. These must be picked such that the force placed on the micro particles are enough to overcome the forces imposed by the flow rate of the water and reach the nodes by the exit of the filter. The placement and construction of the transducers will be done based on the size of the filter enclosure, such that only 2 nodes are present for each of pair of transducers. This would require $\lambda/2$ to be near a diameter of the filter enclosure. For a two inch enclosure a resonant frequency of around 16 kHz would be required. Other frequencies could be used to optimize node placement. As the effluent travels to the exit of the separating filter the micro plastics will be aligned to exit through a separate channel than the central channel, which should have water without plastics. Some embodiments might use a check valve system on the exits to prevent contamination due to backflow. The transducers could be constructed from a single piezo element, a langevin stack, or other known methods in the art.

Figure 26:
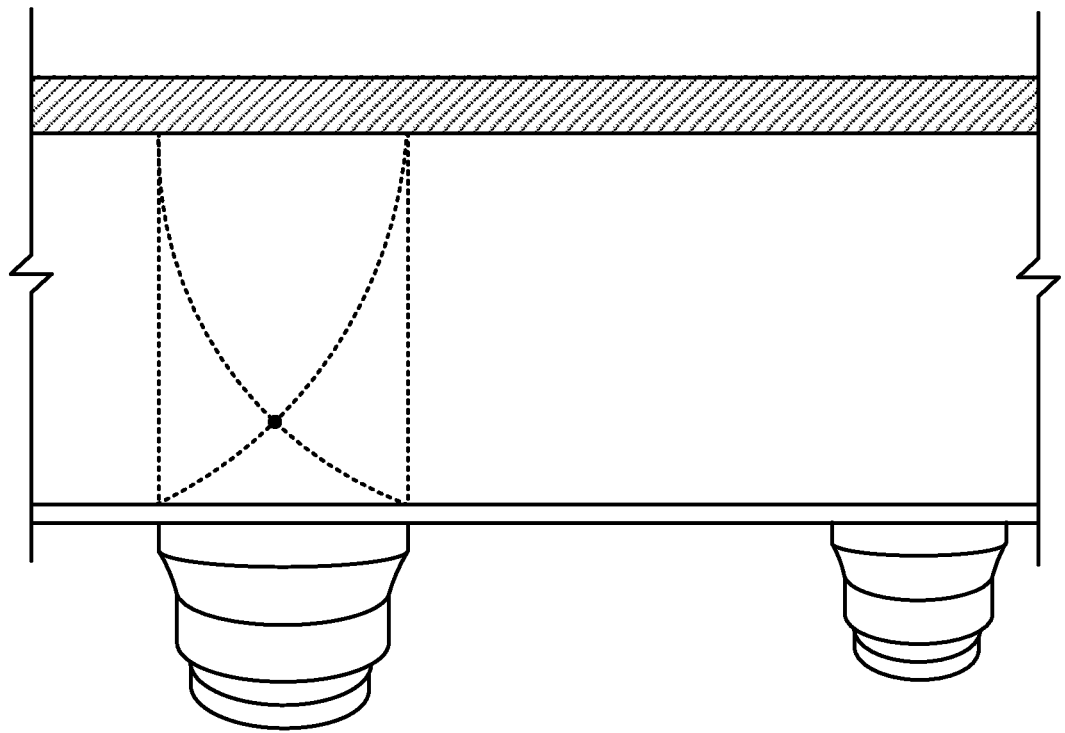
FIG. 26 is an illustration of a microplastic filtrations including a single transducer to create a single node.

An alternative embodiment, as best shown in FIG. 26, uses a single transducer to create a single node instead of multiple transducers to create the standing wave. To prevent reflections in the enclosure, which could create unwanted nodes, acoustic absorbing material would be placed on one or more of the enclosure walls. This embodiment would also have multiple exit channels to allow for cleaned effluent to be separated from the micro plastics. The frequency and energy density of this embodiment would be selected to ensure that a single node is crated and the pressure was great enough to overcome the force of water flow. Similar embodiments may have a series of one or more standing wave.

Figure 27:
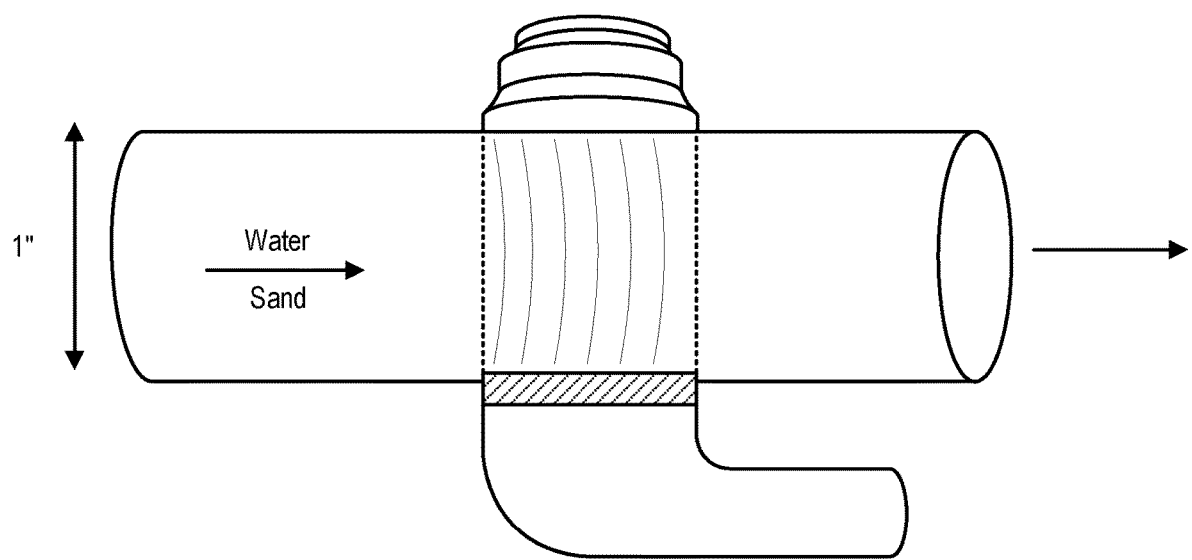
FIG. 27 is an illustration of a microplastic filtration system relying on a standing pressure wave.

Another embodiment, as best shown in FIG. 27, would not rely on nodes for the separation, but would just rely on the standing pressure wave created in a section of the filter. This requires either a lower frequency for the transducer to operate or a reduction in the pipe or enclosure size, such as a less than 20 kHz for a 1" diameter filter, velocity of 1500 ms, and a $\lambda$ of 3" ($\lambda/2$ of 1.5"). The $\lambda/2$ needs to be greater than the diameter to prevent nodes. The transducer would be powered at a level that the pressure in the standing wave was enough to overcome water flow, forcing heavier density particles out into a secondary channel. A filter could be placed at an entry to this channel or further down the channel. It may be desirable to have an angle in the channel to cause reflections from the standing wave to be reflected into the exit of the channel. Alternatively, the filter may have acoustic absorbing properties, or acoustic absorbing materials could be placed in the exit channel. The frequency should be chosen to ensure that there is are no nodes in the flow of the effluent. It is considered that the implementation could have a series of transducers in this configuration to create a uniform pressure field in the desired area.

In all embodiments, the channel or outlet with the micro plastics could be directed to a filter or collection tank. Filters could use a single or combination of methods to collect the micro plastics including but not limited to charcoal filters, reverse osmosis, electrostatic, water ionizers, and other filters known in the art. Heat could also be used to combine the micro plastic particles into larger particles, which would be easier to filter. The heat could be through conduction through the water, or contact with a heated plate or grid. It is also considered that ultrasound could be used to join the plastics. This could be done through traditional welding methods, or through HIFU. In addition, RF, microwave or other methods could be used. Because many synthetic polymers have a melt temperature higher than the PVC used in plumbing, a cooling tank, refrigeration, or copper pipes must be used to prevent damage to the surrounding structures.

Modifications and variations of the disclosed embodiments are possible without departing from the scope of the invention defined in the appended claims.

The examples described herein are examples only and are provided to assist in the explanation of the apparatuses, devices, systems and methods described herein. None of the features or components shown in the drawings or discussed herein should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. The features illustrated or described in connection with one non-limiting embodiment may be combined with the features of other non-limiting embodiments. Such modifications and variations are intended to be included within the scope of the present disclosure.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While certain examples have been shown and described herein, those of ordinary skill in the art will understand that the examples described herein and illustrated in the accompanying drawings are non-limiting examples. Numerous variations, changes, and substitutions will be apparent to those skilled in the art without departing from the invention. Accordingly, it is intended that the invention be limited only by the scope of the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A robotically enhanced operating table assembly for aiding a surgeon during surgery, the operating table assembly comprising:
   an operating table;
   a robotic attachment affixed to the operating table, wherein the robotic attachment includes a movable robotic arm configured to move relative to the operating table to position a joint of a patient on the operating table during surgery, and a motor operably coupled to the robotic arm and configured to control movement of the robotic arm relative to the operating table to position the joint of the patient on the operating table during surgery; and
   a console operably connected to the robotic attachment to enable an operator to control movement of the robotic attachment relative to the operating table during surgery.

2. The operating table assembly of claim 1, wherein the robotic attachment further includes a camera.

3. The operating table assembly of claim 1, wherein the robotic attachment is configured to position the joint of the patient in relation to a reference point.

4. The operating table assembly of claim 3, wherein the robotic attachment performs movements of the joint of the patient relative to the operating table in millimeter increments.

5. The operating table assembly of claim 3, wherein the robotic attachment is configured to move the joint of the patient relative to the table by applying at least one of traction, torque, push-force, or pressure.

6. The operating table assembly of claim 3, wherein the reference point is a portion of a surgical room configured to house the operating table.

7. The operating table assembly of claim 3, wherein the reference point is located on the surgeon.

8. The operating table assembly of claim 1, further comprising virtual reality, wherein the virtual reality displays particular regions of the patient to aid in determining a desired position of the joint of the patient.

9. The operating table assembly of claim 1, wherein the motor is powered mechanically, electrically, pneumatically, or hydraulically.

10. The operating table assembly of claim 1, wherein the motor is a servo motor configured to move the robotic arm with precise movements.

11. The operating table assembly of claim 1, wherein the motor is a piezo crystal configured to operate the robotic arm with fine movements.

12. The operating table assembly of claim 1, further comprising a GPS, the GPS being located on a portion of the robotic attachment, the GPS being configured to locate personnel location during surgery.

13. The operating table assembly of claim 1, wherein the attachment includes an imaging component, the imaging component being configured to scan the joint of the patient to produce a scan viewable to the surgeon.

14. The operating table assembly of claim 13, wherein the imaging component is micro ultra sounds imagining.

15. The operating table assembly of claim 1, wherein the console is further configured to send commands to the robotic attachment, wherein the commands define position parameters for the robotic attachment.

16. The operating table assembly of claim 1, wherein the robotic attachment further includes a robotic retractor configured to retract tissue of the patient during surgery.

17. The operating table assembly of claim 1, wherein the movable robotic arm is configured to move relative to the operating table to position a knee joint of the patient on the operating table during surgery.

18. The operating table assembly of claim 17, wherein the movable robotic arm is configured to move relative to the operating table to impart flexion or extension of the knee joint of the patient on the operating table during surgery.

19. The operating table assembly of claim 1, wherein the movable robotic arm is configured to move relative to the operating table to position a shoulder joint of the patient on the operating table during surgery.

* * * * *